(12) United States Patent
Dillingham et al.

(10) Patent No.: US 9,120,850 B2
(45) Date of Patent: Sep. 1, 2015

(54) BIOSENSOR FOR DETECTION AND VISUALISATION OF SINGLE-STRANDED DNA

(75) Inventors: Mark Dillingham, London (GB); Stephen C. Kowalczykowski, Davis, CA (US); Martin Webb, London (GB)

(73) Assignees: MEDICAL RESEARCH COUNCIL, Swindon (GB); THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 600 days.

(21) Appl. No.: 12/451,954

(22) PCT Filed: Jun. 11, 2008

(86) PCT No.: PCT/GB2008/001995
§ 371 (c)(1),
(2), (4) Date: Apr. 5, 2010

(87) PCT Pub. No.: WO2008/152379
PCT Pub. Date: Dec. 18, 2008

(65) Prior Publication Data
US 2011/0177501 A1    Jul. 21, 2011

(30) Foreign Application Priority Data
Jun. 12, 2007  (GB) .................... 0711328.5

(51) Int. Cl.
*C07K 1/00* (2006.01)
*A61K 39/108* (2006.01)
*C07K 14/245* (2006.01)
*G01N 33/53* (2006.01)
*G01N 33/533* (2006.01)

(52) U.S. Cl.
CPC ............ *C07K 14/245* (2013.01); *G01N 33/533* (2013.01); *G01N 33/5308* (2013.01); *G01N 2500/00* (2013.10)

(58) Field of Classification Search
USPC ................................ 530/350; 424/241.1, 9.6
See application file for complete search history.

(56) References Cited

U.S. PATENT DOCUMENTS 6,746,849 B1    6/2004  Brune et al.
2005/0037377 A1    2/2005  Le

OTHER PUBLICATIONS

Jose et al (ChemBioChem. 2003. 4:396-405).*
Mikayama et al. (Nov. 1993. Proc.Natl.Acad.Sci. USA, vol. 90 : 10056-10060).*
Rudinger et al. (Jun. 1976. Peptide Hormones. Biol.Council. pp. 5-7).*
http://en.wikipedia.org/wiki/Cysteine. 2005.*
J. Chen et al., "The Role of the 6 Lysines and the Terminal Amine of *Escherichia coli* Single-Strand Binding Protein in its Binding of Single-Stranded DNA", Protein Science, vol. 7, pp. 1781-1788, 1998.
S. V. Kuznetsov et al., "Microsecond Dynamics of Protein-DNA Interactions: Direct Observation of the Wrapping/Unwrapping Kinetics of Single-stranded DNA around the *E. coli* SSB Tetramer", Journal of Molecular Biology, vol. 359, pp. 55-65, 2006.
Abstract 111:149330 from the Chemical Abstracts Database, 1988.
N. Morin et al., "Mutations that Affect Phosphorylation of the Adenovirus DNA-Binding Protein Alter its Ability to Enhance its Own Synthesis", Journal of Virology, vol. 63, No. 12, pp. 5228-5237, Dec. 1989.
Qian-Hong Wan and X. Chris Le, "Studies of protein—DNA interactions by capillary electrophoresis/laser-induced fluorescence polarization", Anal Chem, Nov. 15, 2000;72(22):5583-9.

\* cited by examiner

*Primary Examiner* — Jennifer Graser
(74) *Attorney, Agent, or Firm* — Wenderoth, Lind & Ponack, L.L.P.

(57) ABSTRACT

A modified protein of the single strand DNA-binding domain, SSB family comprising a detectable label is disclosed. The label has detectable characteristics which alter on binding single stranded DNA. The protein is thus useful in an assay for single stranded DNA.

9 Claims, 9 Drawing Sheets

FIG. 8

```
Escherichia coli 1790494              MASRGVNKVILVGNLGQDPEVRYMPNGGAVANITLATSESWRDKATGEMKEQTEWHRVVL
Enterobacteria phage P1 46401640      MAQRGVNKVILIGTLGQDPEIRYIPNGGAVGRLSIATNESWRDKQTGQQKEQTEWHKVVL
Salmonella typhimurium 20521565       MSARGINKVILVGRLGNDPEVRYIPNGGAVANLQVATSESWRDKQTGEMREQTEWHRVVL
Bacillus licheniformis 52350536       ----MLNRVVLVGRLTKDPELRYTPSGAAVATFTLAVNRTFTNQQG---EREADFINCVV
Campylobacter jejuni 24115640         ------MNQVNLCGYLGKDFELKYTPNGSAFAKTTLGVSENRRNEKG-EYEAYTSWIPIL
Pseudomonas syringae 38257082         -MARGINKVILVGTCGQDPDCRYLPNGTAVTNLSLATSEQWTDKQSGQKVEKTEWHRVSL
Listeria innocua 16799117             ----MMNRVVLVGRLTKDPELRYTPAGVAVATFTLAVNRTFTNQQG---EREADFINCVV Escherichia coli 1790494              FGKLAEVASEYLRKGSQVYIEGQLRTRKWTDQSGQDRYTTEVVNVGGTMQMLGGRQGGG
Enterobacteria phage P1 46401640      FGKLAEIASEYLRKGSQVYIEGKLKTRKWTDDAGVERYTTEIIVSQGGTMQMIGARRDD
Salmonella typhimurium 20521565       FGKLAEVAGEYLRKGAQVYIEGQLRTRSWDDN-GITRYITEILVKTTGTMQMLGSAPQQN
Bacillus licheniformis 52350536       WRRQAENVANFLKKGSLAGVDGRLQTRSYENQQGQRVYVTEVQAESVQFLEPKG--GGSG
Campylobacter jejuni 24115640         FGRKAEVANQYIKKGDRFLGTGKIVTSSYTDQYGNIRYGWQVISSFEFIEKKAEQNQD
Pseudomonas syringae 38257082         FGKVAEIAGEYLRKGSQVYIEGKLQTREWEKD-GIKRYTTEIVDMQGTMQLLGGRPQGD
Listeria innocua 16799117             WRKPAENVANFLKKGSMAGVDGRVQTRNYEGNDGKRVYVTEIVAESVQFLEPRNSNGGGG
```

| | |
|---|---|
| Escherichia coli 1790494 | A---PAGGNIGGGQPQGGWGQPQPQGGNQFS-GGAQS--RPQQSAPAAPSNEPP---- |
| Enterobacteria phage P1 46401640 | --------SQSSNGWGQSNQPQNHQQYS-GGG----KPQSNA----NNEPP---- |
| Salmonella typhimurium 20521565 | --------AQAQPKPQQNGQPQSADATKKGGAKTKGRGRKAAQPEPQPQTPEGE-D |
| Bacillus licheniformis 52350536 | S--------GGYSGGQ-------GGQHFGGGQNEPAPFGGSQNNQNRNQGNSFNDDPFANDG |
| Campylobacter jejuni 24115640 | -----------------YKGEPQPNQITP--------PKEAETMQSIDENQ---AE |
| Pseudomonas syringae 38257082 | SQHSQNGQGSGDSDHQEPPRQQAPQQAAPEKPSGKGKAAPKPPRASGKQAQAKAPAPQPA |
| Listeria innocua 16799117 | N--------NNYQGGNNNNNYNNGGNNFGQAPTNNGGFGQDQQQSQNQNYQSTNNDPFASDG |
| | |
| Escherichia coli 1790494 | MDFD---DDIPF |
| Enterobacteria phage P1 46401640 | MDFD---DDIPF |
| Salmonella typhimurium 20521565 | YGFS---DDIPF |
| Bacillus licheniformis 52350536 | KPIDISDDDLPF |
| Campylobacter jejuni 24115640 | TYMQ-DDENLPF |
| Pseudomonas syringae 38257082 | GDFDGGDDNIPFMDPYRFNWMLV |
| Listeria innocua 16799117 | KPIDISDDDLPF |

FIG. 8(CONTD.)

SEQUENCE LISTING

```
<160> NUMBER OF SEQ ID NOS: 12

<210> SEQ ID NO 1
<211> LENGTH: 178
<212> TYPE: PRT
<213> ORGANISM: Escherichia coli

<400> SEQUENCE: 1

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
            20                  25                  30

Ile Thr Leu Ala Thr Ser Glu Ser Trp Arg Asp Lys Ala Thr Gly Glu
        35                  40                  45

Met Lys Glu Gln Thr Glu Trp His Arg Val Val Leu Phe Gly Lys Leu
    50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
            100                 105                 110

Leu Gly Gly Arg Gln Gly Gly Gly Ala Pro Ala Gly Gly Asn Ile Gly
        115                 120                 125

Gly Gly Gln Pro Gln Gly Gly Trp Gly Gln Pro Gln Pro Gln Gly
    130                 135                 140
```

```
Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe

<210> SEQ ID NO 2
<211> LENGTH: 178
<212> TYPE: PRT
<213> ORGANISM: Artificial Sequence
<220> FEATURE:
<223> OTHER INFORMATION: Synthetic construct; SEQ ID NO:1 comprising
      the mutation S92C

<400> SEQUENCE: 2

Met Ala Ser Arg Gly Val Asn Lys Val Ile Leu Val Gly Asn Leu Gly
1               5                   10                  15

Gln Asp Pro Glu Val Arg Tyr Met Pro Asn Cys Gly Ala Val Ala Asn
                20                  25                  30

Ile Thr Leu Ala Thr Ser Glu Ser Trp Arg Asp Lys Ala Thr Gly Glu
            35                  40                  45

Met Lys Glu Gln Thr Glu Trp His Arg Val Val Leu Phe Gly Lys Leu
50                  55                  60

Ala Glu Val Ala Ser Glu Tyr Leu Arg Lys Gly Ser Gln Val Tyr Ile
65                  70                  75                  80

Glu Gly Gln Leu Arg Thr Arg Lys Trp Thr Asp Gln Ser Gly Gln Asp
                85                  90                  95

Arg Tyr Thr Thr Glu Val Val Val Asn Val Gly Gly Thr Met Gln Met
                100                 105                 110

Leu Gly Gly Arg Gln Gly Gly Gly Ala Pro Ala Gly Gly Asn Ile Gly
            115                 120                 125

Gly Gly Gln Pro Gln Gly Gly Trp Gly Gln Pro Gln Gln Pro Gln Gly
            130                 135                 140

Gly Asn Gln Phe Ser Gly Gly Ala Gln Ser Arg Pro Gln Gln Ser Ala
145                 150                 155                 160

Pro Ala Ala Pro Ser Asn Glu Pro Pro Met Asp Phe Asp Asp Asp Ile
                165                 170                 175

Pro Phe

<210> SEQ ID NO 3
<211> LENGTH: 178
<212> TYPE: PRT
<213> ORGANISM: Artificial Sequence
<220> FEATURE:
<223> OTHER INFORMATION: Synthetic construct; SEQ ID NO:1 comprising
      the mutation G26C

<400> SEQUENCE: 3

Met Ala Ser Arg Gly Val Asn Lys Val Ile Leu Val Gly Asn Leu Gly
1               5                   10                  15

Gln Asp Pro Glu Val Arg Tyr Met Pro Asn Gly Gly Ala Val Ala Asn
                20                  25                  30

Ile Thr Leu Ala Thr Ser Glu Ser Trp Arg Asp Lys Ala Thr Gly Glu
            35                  40                  45

Met Lys Glu Gln Thr Glu Trp His Arg Val Val Leu Phe Gly Lys Leu
50                  55                  60

Ala Glu Val Ala Ser Glu Tyr Leu Arg Lys Gly Ser Gln Val Tyr Ile
```

65                  70                  75                  80
Glu Gly Gln Leu Arg Thr Arg Lys Trp Thr Asp Gln Cys Gly Gln Asp
                    85                  90                  95
Arg Tyr Thr Thr Glu Val Val Val Asn Val Gly Gly Thr Met Gln Met
                100                 105                 110
Leu Gly Gly Arg Gln Gly Gly Gly Ala Pro Ala Gly Gly Asn Ile Gly
            115                 120                 125
Gly Gly Gln Pro Gln Gly Gly Trp Gly Gln Pro Gln Gln Pro Gln Gly
        130                 135                 140
Gly Asn Gln Phe Ser Gly Gly Ala Gln Ser Arg Pro Gln Gln Ser Ala
145                 150                 155                 160
Pro Ala Ala Pro Ser Asn Glu Pro Pro Met Asp Phe Asp Asp Asp Ile
                165                 170                 175

Pro Phe

<210> SEQ ID NO 4
<211> LENGTH: 178
<212> TYPE: PRT
<213> ORGANISM: Artificial Sequence
<220> FEATURE:
<223> OTHER INFORMATION: Synthetic construct; SEQ ID NO:1 comprising
      the mutation W88C

<400> SEQUENCE: 4

Met Ala Ser Arg Gly Val Asn Lys Val Ile Leu Val Gly Asn Leu Gly
1               5                   10                  15
Gln Asp Pro Glu Val Arg Tyr Met Pro Asn Gly Gly Ala Val Ala Asn
                20                  25                  30
Ile Thr Leu Ala Thr Ser Glu Ser Trp Arg Asp Lys Ala Thr Gly Glu
            35                  40                  45
Met Lys Glu Gln Thr Glu Trp His Arg Val Val Leu Phe Gly Lys Leu
        50                  55                  60
Ala Glu Val Ala Ser Glu Tyr Leu Arg Lys Gly Ser Gln Val Tyr Ile
65                  70                  75                  80
Glu Gly Gln Leu Arg Thr Arg Lys Cys Thr Asp Gln Ser Gly Gln Asp
                85                  90                  95
Arg Tyr Thr Thr Glu Val Val Val Asn Val Gly Gly Thr Met Gln Met
                100                 105                 110
Leu Gly Gly Arg Gln Gly Gly Gly Ala Pro Ala Gly Gly Asn Ile Gly
            115                 120                 125
Gly Gly Gln Pro Gln Gly Gly Trp Gly Gln Pro Gln Gln Pro Gln Gly
        130                 135                 140
Gly Asn Gln Phe Ser Gly Gly Ala Gln Ser Arg Pro Gln Gln Ser Ala
145                 150                 155                 160
Pro Ala Ala Pro Ser Asn Glu Pro Pro Met Asp Phe Asp Asp Asp Ile
                165                 170                 175

Pro Phe

<210> SEQ ID NO 5
<211> LENGTH: 70
<212> TYPE: DNA
<213> ORGANISM: Artificial Sequence
<220> FEATURE:
<223> OTHER INFORMATION: Synthetic construct; dT70

<400> SEQUENCE: 5
tttttttttt tttttttttt tttttttttt tttttttttt tttttttttt tttttttttt       60

<210> SEQ ID NO 6
<211> LENGTH: 177
<212> TYPE: PRT
<213> ORGANISM: Escherichia coli

<400> SEQUENCE: 6

Ala Ser Arg Gly Val Asn Lys Val Ile Leu Val Gly Asn Leu Gly Gln
1               5                   10                  15

Asp Pro Glu Val Arg Tyr Met Pro Asn Gly Gly Ala Val Ala Asn Ile
            20                  25                  30

Thr Leu Ala Thr Ser Glu Ser Trp Arg Asp Lys Ala Thr Gly Glu Met
        35                  40                  45

Lys Glu Gln Thr Glu Trp His Arg Val Val Leu Phe Gly Lys Leu Ala
    50                  55                  60

Glu Val Ala Ser Glu Tyr Leu Arg Lys Gly Ser Gln Val Tyr Ile Glu
65                  70                  75                  80

Gly Gln Leu Arg Thr Arg Lys Trp Thr Asp Gln Ser Gly Gln Asp Arg
                85                  90                  95

Tyr Thr Thr Glu Val Val Val Asn Val Gly Gly Thr Met Gln Met Leu
            100                 105                 110

Gly Gly Arg Gln Gly Gly Gly Ala Pro Ala Gly Asn Ile Gly Gly
        115                 120                 125

Gly Gln Pro Gln Gly Gly Trp Gly Gln Pro Gln Pro Gln Gly Gly
    130                 135                 140

Asn Gln Phe Ser Gly Gly Ala Gln Ser Arg Pro Gln Gln Ser Ala Pro
145                 150                 155                 160

Ala Ala Pro Ser Asn Glu Pro Pro Met Asp Phe Asp Asp Asp Ile Pro
                165                 170                 175

Phe

<210> SEQ ID NO 7
<211> LENGTH: 162
<212> TYPE: PRT
<213> ORGANISM: Enterobacter phage P1

<400> SEQUENCE: 7

Met Ala Gln Arg Gly Val Asn Lys Val Ile Leu Ile Gly Thr Leu Gly
1               5                   10                  15

Gln Asp Pro Glu Ile Arg Tyr Ile Pro Asn Gly Gly Ala Val Gly Arg
            20                  25                  30

Leu Ser Ile Ala Thr Asn Glu Ser Trp Arg Asp Lys Gln Thr Gly Gln
        35                  40                  45

Gln Lys Glu Gln Thr Glu Trp His Lys Val Val Leu Phe Gly Lys Leu
    50                  55                  60

Ala Glu Ile Ala Ser Glu Tyr Leu Arg Lys Gly Ser Gln Val Tyr Ile
65                  70                  75                  80

Glu Gly Lys Leu Lys Thr Arg Lys Trp Thr Asp Asp Ala Gly Val Glu
                85                  90                  95

Arg Tyr Thr Thr Glu Ile Ile Val Ser Gln Gly Gly Thr Met Gln Met
            100                 105                 110

Ile Gly Ala Arg Arg Asp Asp Ser Gln Ser Asn Gly Trp Gly Gln
        115                 120                 125

Ser Asn Gln Pro Gln Asn His Gln Gln Tyr Ser Gly Gly Gly Lys Pro

```
                 130                 135                 140
Gln Ser Asn Ala Asn Asn Glu Pro Pro Met Asp Phe Asp Asp Asp Ile
145                 150                 155                 160

Pro Phe

<210> SEQ ID NO 8
<211> LENGTH: 175
<212> TYPE: PRT
<213> ORGANISM: Salmonella typhimurium

<400> SEQUENCE: 8

Met Ser Ala Arg Gly Ile Asn Lys Val Ile Leu Val Gly Arg Leu Gly
1               5                   10                  15

Asn Asp Pro Glu Val Arg Tyr Ile Pro Asn Gly Gly Ala Val Ala Asn
                20                  25                  30

Leu Gln Val Ala Thr Ser Glu Ser Trp Arg Asp Lys Gln Thr Gly Glu
            35                  40                  45

Met Arg Glu Gln Thr Glu Trp His Arg Val Val Leu Phe Gly Lys Leu
        50                  55                  60

Ala Glu Val Ala Gly Glu Tyr Leu Arg Lys Gly Ala Gln Val Tyr Ile
65                  70                  75                  80

Glu Gly Gln Leu Arg Thr Arg Ser Trp Asp Asp Asn Gly Ile Thr Arg
                85                  90                  95

Tyr Ile Thr Glu Ile Leu Val Lys Thr Thr Gly Thr Met Gln Met Leu
                100                 105                 110

Gly Ser Ala Pro Gln Gln Asn Ala Gln Ala Gln Pro Lys Pro Gln Gln
            115                 120                 125

Asn Gly Gln Pro Gln Ser Ala Asp Ala Thr Lys Lys Gly Gly Ala Lys
        130                 135                 140

Thr Lys Gly Arg Gly Arg Lys Ala Ala Gln Pro Glu Pro Gln Pro Gln
145                 150                 155                 160

Thr Pro Glu Gly Glu Asp Tyr Gly Phe Ser Asp Ile Pro Phe
                165                 170                 175

<210> SEQ ID NO 9
<211> LENGTH: 170
<212> TYPE: PRT
<213> ORGANISM: Bacillus licheniformis

<400> SEQUENCE: 9

Met Leu Asn Arg Val Val Leu Val Gly Arg Leu Thr Lys Asp Pro Glu
1               5                   10                  15

Leu Arg Tyr Thr Pro Ser Gly Ala Ala Val Ala Thr Phe Thr Leu Ala
                20                  25                  30

Val Asn Arg Thr Phe Thr Asn Gln Gln Gly Glu Arg Glu Ala Asp Phe
            35                  40                  45

Ile Asn Cys Val Val Trp Arg Arg Gln Ala Glu Asn Val Ala Asn Phe
        50                  55                  60

Leu Lys Lys Gly Ser Leu Ala Gly Val Asp Gly Arg Leu Gln Thr Arg
65                  70                  75                  80

Ser Tyr Glu Asn Gln Gln Gly Gln Arg Val Tyr Val Thr Glu Val Gln
                85                  90                  95

Ala Glu Ser Val Gln Phe Leu Glu Pro Lys Gly Gly Gly Ser Gly Ser
                100                 105                 110

Gly Gly Tyr Ser Gly Gly Gln Gly Gly Gln His Phe Gly Gly Gly Gln
            115                 120                 125
```

Asn Glu Pro Ala Pro Phe Gly Gly Ser Gln Asn Asn Gln Asn Arg Asn
          130                 135                 140

Gln Gly Asn Ser Phe Asn Asp Asp Pro Phe Ala Asn Asp Gly Lys Pro
145                 150                 155                 160

Ile Asp Ile Ser Asp Asp Leu Pro Phe
              165                 170

<210> SEQ ID NO 10
<211> LENGTH: 152
<212> TYPE: PRT
<213> ORGANISM: Campylobacter jejuni

<400> SEQUENCE: 10

Met Asn Gln Val Asn Leu Cys Gly Tyr Leu Gly Lys Asp Phe Glu Leu
1               5                   10                  15

Lys Tyr Thr Pro Asn Gly Ser Ala Phe Ala Lys Thr Thr Leu Gly Val
              20                  25                  30

Ser Glu Asn Arg Arg Asn Glu Lys Gly Glu Tyr Glu Ala Tyr Thr Ser
          35                  40                  45

Trp Ile Pro Ile Ile Leu Phe Gly Arg Lys Ala Glu Val Ala Asn Gln
50                  55                  60

Tyr Ile Lys Lys Gly Asp Arg Phe Leu Gly Thr Gly Lys Ile Val Thr
65                  70                  75                  80

Ser Ser Tyr Thr Asp Gln Tyr Gly Asn Ile Arg Tyr Gly Trp Gln Val
              85                  90                  95

Val Ile Ser Ser Phe Glu Phe Ile Glu Lys Lys Ala Glu Gln Asn Gln
          100                 105                 110

Asp Tyr Lys Gly Glu Pro Gln Pro Asn Gln Ile Thr Pro Pro Lys Glu
      115                 120                 125

Ala Glu Thr Met Gln Ser Ile Asp Glu Asn Gln Ala Glu Ile Tyr Met
  130                 135                 140

Gln Asp Asp Glu Asn Leu Pro Phe
145                 150

<210> SEQ ID NO 11
<211> LENGTH: 201
<212> TYPE: PRT
<213> ORGANISM: Pseudomonas syringae

<400> SEQUENCE: 11

Met Ala Arg Gly Ile Asn Lys Val Ile Leu Val Gly Thr Cys Gly Gln
1               5                   10                  15

Asp Pro Asp Cys Arg Tyr Leu Pro Asn Gly Thr Ala Val Thr Asn Leu
              20                  25                  30

Ser Leu Ala Thr Ser Glu Gln Trp Thr Asp Lys Gln Ser Gly Gln Lys
          35                  40                  45

Val Glu Lys Thr Glu Trp His Arg Val Ser Leu Phe Gly Lys Val Ala
      50                  55                  60

Glu Ile Ala Gly Glu Tyr Leu Arg Lys Gly Ser Gln Val Tyr Ile Glu
65                  70                  75                  80

Gly Lys Leu Gln Thr Arg Glu Trp Glu Lys Asp Gly Ile Lys Arg Tyr
              85                  90                  95

Thr Thr Glu Ile Val Val Asp Met Gln Gly Thr Met Gln Leu Leu Gly
          100                 105                 110

Gly Arg Pro Gln Gly Asp Ser Gln His Ser Gln Asn Gly Gln Gly Ser
      115                 120                 125

```
Gly Asp Ser Asp His Gln Glu Pro Pro Arg Gln Gln Ala Pro Gln Gln
        130                 135                 140

Ala Ala Pro Glu Lys Pro Ser Gly Lys Gly Lys Ala Ala Pro Lys Pro
145                 150                 155                 160

Pro Arg Ala Ser Gly Lys Gln Ala Gln Ala Lys Ala Pro Ala Pro Gln
                165                 170                 175

Pro Ala Gly Asp Phe Asp Gly Gly Asp Asp Asn Ile Pro Phe Met Asp
            180                 185                 190

Pro Tyr Arg Phe Asn Trp Met Leu Val
            195                 200

<210> SEQ ID NO 12
<211> LENGTH: 179
<212> TYPE: PRT
<213> ORGANISM: Listeria innocua

<400> SEQUENCE: 12

Met Met Asn Arg Val Val Leu Val Gly Arg Leu Thr Lys Asp Pro Glu
1               5                   10                  15

Leu Arg Tyr Thr Pro Ala Gly Val Ala Val Ala Thr Phe Thr Leu Ala
                20                  25                  30

Val Asn Arg Thr Phe Thr Asn Gln Gln Gly Glu Arg Glu Ala Asp Phe
            35                  40                  45

Ile Asn Cys Val Val Trp Arg Lys Pro Ala Glu Asn Val Ala Asn Phe
        50                  55                  60

Leu Lys Lys Gly Ser Met Ala Gly Val Asp Gly Arg Val Gln Thr Arg
65                  70                  75                  80

Asn Tyr Glu Gly Asn Asp Gly Lys Arg Val Tyr Val Thr Glu Ile Val
                85                  90                  95

Ala Glu Ser Val Gln Phe Leu Glu Pro Arg Asn Ser Asn Gly Gly Gly
                100                 105                 110

Gly Asn Asn Asn Tyr Gln Gly Gly Asn Asn Asn Asn Tyr Asn Asn
            115                 120                 125

Gly Gly Asn Asn Phe Gly Gln Ala Pro Thr Asn Asn Gly Gly Phe Gly
        130                 135                 140

Gln Asp Gln Gln Gln Ser Gln Asn Gln Asn Tyr Gln Ser Thr Asn Asn
145                 150                 155                 160

Asp Pro Phe Ala Ser Asp Gly Lys Pro Ile Asp Ile Ser Asp Asp Asp
                165                 170                 175

Leu Pro Phe
```

BIOSENSOR FOR DETECTION AND VISUALISATION OF SINGLE-STRANDED DNA

This application is a U.S. national stage of International Application No. PCT/GB2008/001995 filed Jun. 11, 2008.

All documents cited herein are incorporated by reference in their entirety.

TECHNICAL FIELD

This invention relates to assays for single stranded DNA, particularly the detection and visualisation of single stranded DNA in biological solutions. More particularly, the present invention relates to a modified protein of the single strand DNA-binding domain, SSB family, and to the use of such a protein in a biological assay.

BACKGROUND ART

The formation and maintenance of single-stranded DNA (ssDNA) is an important part of many processes involving DNA. For instance, strand separation of double-stranded DNA (dsDNA) is catalyzed by helicases and this exposure of the bases on the DNA allows further processing, such as repair or replication. Assays of helicase activity are an important part of probing the related biological processes.

Although there are methods to measure ssDNA, as opposed to dsDNA, in real time assays, sensitivity and time resolution have been limited. Generally, fluorescence-based assays have provided the combination of high sensitivity and time resolution required for these types of measurement. There are several dyes that provide fluorescence signals to monitor dsDNA to ssDNA transformation [1,2], but many bind specifically in the grooves of dsDNA and the fluorescence decreases on release from the DNA as strand separation occurs. This type of probe may not be suitable for low extents of reaction, as it relies on measuring a small decrease of fluorescence against a large background. In addition, dyes that bind to double stranded DNA may inhibit enzymes acting on such DNA.

Obtaining a quantitative signal change combined with specificity for the ssDNA and discrimination against other similar molecules, such as dsDNA, that may be present in the assay provides a considerable scientific challenge.

DISCLOSURE OF THE INVENTION

In the present invention, it has been shown that modification of a protein of the single strand DNA-binding domain, SSB family (hereinafter referred to simply as SSB) in order to attach a fluorescent label, results in a modified SSB which is able to act as a biosensor without requiring cofactors. SSB interacts with single stranded DNA and unwound double stranded DNA. The modified protein may be used in kinetic assays with high sensitivity and time resolution to probe dsDNA unwinding, for example in real time assays of DNA helicase activity in vitro or in applications such as single molecule studies and high throughput assays.

Thus the invention provides a modified SSB comprising at least one detectable label attached to an amino acid of the protein.

An intrinsic fluorescence change has been observed before in relation to SSB. There is a tryptophan fluorescence decrease when SSB binds to DNA and this has been used as a probe for DNA strand separation [3] and SSB-DNA interactions [15]. However, these assays demonstrate one-two orders of magnitude less sensitivity than the use of the modified SSB of the present invention. Furthermore, assays relying on the intrinsic tryptophan fluorescence changes have limitations due to photobleaching and interference from other species that absorb in the same UV range as tryptophan.

Biosensors that do not require cofactors and based on fluorescent proteins have been successful in a number of cases to provide rapid probes of concentration of molecules in biological assays. Such biosensors interact with the molecule of interest giving a fluorescence signal change. There are several examples of this type of reagentless biosensors, such as for phosphate [4], glucose [5] and maltose [6]. Several reviews describe this general approach [7, 8 and 9].

The Single Strand DNA-Binding Domain Protein Family

The single strand DNA-binding domain protein family (SSB family) is an example of a family of proteins that interact with single stranded DNA and unwound double stranded DNA. This family of proteins is defined in the SCOP database [10] and has an all-beta structure with an OB fold (barrel, closed; n=5, S=10). It is family 50263. This family is distinct from SCOP family 50315 which has a structure of an OB fold (barrel, open; n*=5, S*=8). The SSB family of proteins play essential roles in DNA replication, recombination and repair both in prokaryotes and eukaryotes. Members of this family of proteins have been investigated from several prokaryotic organisms and there are structures of the protein from *Escherichia coli* in the presence and absence of DNA.

SSB may be eukaryotic or prokaryotic. Prokaryotic SSB may be bacterial. Examples of bacterial SSBs include those aligned in FIG. 8, such as *E. coli, Salmonella typhimurium, Bacillus licheniformis, Campylobacter jejuni, Pseudomonas syringae* and *Listeria innocua*, as well as *T. aquaticus, M. smegmatis* and *D. radiodurans*.

Preferably, the modified SSB of the present invention is a modified *E. coli* SSB protein. The sequence of native *E. coli* SSB is as follows (accession number gi1790494; SEQ ID NO: 1 herein):

```
MASRGVNKVILVGNLGQDPEVRYMPNGGAVANITLATSESWRDKATGEM

KEQTEWHRVVLFGKLAEVASEYLRKGSQVYIEGQLRTRKWTDQSGQDRY

TTEVVVNVGGTMQMLGGRQGGGAPAGGNIGGGQPQGGWGQPQQPQGGNQ

FSGGAQSRPQQSAPAAPSNEPPMDFDDDIPF.
```

The N-terminal methionine is removed during expression to give the mature protein (see SEQ ID NO: 6). The amino-acid numbering used herein relates to the mature protein starting at Ala-2 of SEQ ID NO: 1.

SSB from *E. coli* is encoded by the ssb gene of *E. coli*. It exists as a stable tetramer that can bind a minimum of ~65 bases of DNA at high salt concentrations [11] and the crystal structure shows DNA wrapped around a tetramer [12]. At low salt *E. coli* SSB can bind a ~35 base length of ssDNA. The crystal structure in the absence of DNA shows a different arrangement of monomers within a tetramer [13]. The protein binds DNA rapidly and tightly, but the mechanism may be complex due to the need for the DNA to wrap around *E. coli* SSB [14,15]. Binding is apparently cooperative and there may be interaction between neighbouring SSB oligomers along a strand of ssDNA. There is also evidence that *E. coli* SSB can exist as a monomer at low concentrations and can bind DNA weakly in this state [16].

On binding to single stranded DNA, SSBs may undergo a conformational change. However, the crystal structures of SSB suggest there are only minor changes in protein subunit conformation on association with DNA [12, 13]. In wrapping around the surface of the tetramer, DNA winds through a series of channels in the protein surface.

Labels

The SSB of the invention is modified in order to include a detectable label attached to an amino acid of the protein and whose detectable characteristics alter on binding single stranded DNA. This alteration may, but not necessarily, result from a change in protein conformation. Whether the alteration is due to a change in the protein confirmation or not, the change in the detectable characteristics is due to an alteration in the environment of the label, which is bound to the single stranded DNA binding protein.

Labels used with the invention can give various signals, but preferred labels are luminescent labels. Luminescent labels include both fluorescent and phosphorescent labels. However, the use of other labels is envisaged. For example, electrochemical labels could be used wherein the alteration in the environment of the labels will give rise to a change in redox state. Such a change may be detected using an electrode.

The detectable label is preferably a fluorescent label. The use of fluorescent labels, which may be excited to fluoresce by exposure to certain wavelengths of light, is preferred.

Attachment of the detectable label to the SSB may sometimes reduce the affinity of the protein for single stranded DNA. However, this does not prevent an alteration of the detectable characteristics on binding single stranded DNA which can be quantitatively measured.

Preferably the fluorescent label is a coumarin or a rhodamine.

Shorter excitation wavelengths, such as those of the coumarin labels, are useful in providing a biosensor suitable for measurement of rapid kinetics of single stranded DNA formation, for example in real time assays of DNA helicase activity in vitro. On the other hand, longer excitation wavelengths such as those of the rhodamine fluorophores, which also demonstrate greater photostability, make such a labelled biosensor more suitable for applications such as single molecule studies and high throughput assays. Therefore, labels of the invention may have shorter excitation wavelengths of between about 400-460 nm or longer excitation wavelengths of between about 540-600 nm.

Preferred rhodamine labels are functionalised to give high selectivity for reaction with thiols, such as the haloacetamidotetramethylrhodamine (XATR) molecules, even more preferably iodoacetamidotetramethylrhodamine (IATR) and bromoacetamidotetramethylrhodamine (BATR) molecules. Preferred labels are 5-IATR and 6-IATR The coumarin label is preferably selected from the group consisting of N-[2-(iodoacetamido)ethyl]-7-diethylaminocoumarin-3-carboxamide (IDCC), 2-(4'maleimidylanilino) naphthalene-6-sulfonic acid (MIANS), N-[2-(1-maleimidypethyl]-7-diethylaminocoumarin-3-carboxamide (MDCC), $C_5$-maleimide: xanthylium, 3,6-diamino-9-[2-carboxy-4(or 5)-[[[5-(2,5-dihydro-2,5-dioxo-1H-pyrrol-1-yl) pentyl]amino]carbonyl]phenyl]-4,5-disulfo-, inner salt, monosodium salt (Alexa Fluor 488), and $C_{43}H_{44}Cl_3N_4NaO_{12}S_3$ (Alexa Fluor 546).

When the label is based on coumarin, it is preferably IDCC.

When the label is based on rhodamine, it is preferably 6-IATR.

Attachment of Labels

The SSBs of the present invention have labels attached to their amino acids.

The present invention also provides a method for making a modified SSB which involves modification of a SSB to include a detectable label attached to an amino acid of the protein.

The label may be attached to the SSB by any conventional means known in the art. For example, the label may be attached via amines or carboxyl residues on the protein. However, especially preferred is linkage via thiol groups on cysteine residues.

In a further aspect of the invention, the modified SSB comprises more than one detectable label. In this case, the labels are preferably attached to separate amino acid residues.

In an embodiment of the invention, each monomer of the SSB has the same number of labels attached to it. There may be one label per monomer or alternatively two, three or four labels attached to each monomer.

In a further aspect of the invention, where more than one monomer of the SSB tetramer is modified to include a detectable label, such labels can stack.

If appropriate, natural cysteine residues in the sequence of the SSB may be used for the attachment of the label. However, where no natural cysteine residues are available for label attachment, cysteine residues may be engineered into the sequence of the SSB, preferably by site-directed mutagenesis.

The invention provides a SSB wherein a wild-type non-cysteine residue is replaced by a cysteine residue.

Site-directed mutagenesis will be performed by methods well known in the art for this purpose. Briefly, however, the gene encoding the SSB is isolated, and oligonucleotide probes are constructed to alter by recombination the codon encoding the amino acid which it is desired to change into a codon encoding cysteine. The mutated gene is subsequently expressed, typically in a bacterial expression system, to produce the mutated protein.

The invention also provides a SSB wherein the label is attached to a region of the protein surface. Regions of the protein such as a subunit-subunit interaction surface are not exposed and are thus unsuitable for labelling purposes. Surface located residues are more easily accessible for labelling purposes and are less likely to disrupt the overall shape of the protein when labelled.

Preferably, residues chosen for label attachment are located in a region of the protein surface, which is above a binding channel and on loops of the protein structure. 3D structures of several SSBs are known in the art. The residues chosen are not in a region of the protein which would directly interact with the DNA binding surface per se but are close enough to the DNA surface such that the attached label might be affected by the presence of the DNA. This strategy is a compromise between disrupting DNA binding by, for example, sterically hindering DNA binding (by being "too close") and getting no signal change (by being "too far away"). However, an alteration in the environment of the label may result from a conformational change in a region of the protein to which the label is not directly bound.

Using *E. coli* SSB, suitable residues for label attachment that were above the binding channel but not likely to be involved in protein secondary structure were found on two loops, at approximate residues M23-A28 and K87-Q94. It was also taken into consideration in which direction the wild-type amino acid pointed as this may provide some guidance as to where the label may lie.

Using *E. coli* SSB, the preferred attachment sites for a coumarin label are residue 26 (glycine in the wild type sequence) or residue 92 (serine in the wild type sequence) in the amino acid sequence of *E. coli* SSB. The residues are numbered from the N-terminus of the mature *E. coli* SSB. In the present invention, preferably, either G26 or S92 is converted to cysteine. The *E. coli* SSB of the present invention modified to incorporate a coumarin label has an amino acid sequence selected from SEQ ID NO: 2 and SEQ ID NO: 3 containing the G26C or S92C mutations respectively. Preferably DCC is bonded to the cysteine residue.

Using *E. coli* SSB, the preferred attachment site for a rhodamine label is residue 88 (tryptophan in the wild type sequence) in the amino acid sequence of *E. coli* SSB. The residues are numbered from the N-terminus of the mature *E. coli* SSB. In the present invention preferably, W88 is converted to cysteine. The *E. coli* SSB of the present invention modified to incorporate the rhodamine label has an amino acid sequence as shown in SEQ ID NO:4 containing the W88 mutation. Preferably 6-IATR is bonded to the cysteine residue.

The present invention also provides a modified *E. coli* SSB protein having a sequence of SEQ ID NO:6 comprising the mutation S92C, G26C or W88C.

The corresponding amino acid residues in other SSBs can be identified based on sequence homology for example using the alignment of FIG. 8. It can be observed from FIG. 8 that G26 is conserved in these seven proteins and that position 88 is a hydrophobic aromatic, that is, a tryptophan or a tyrosine in all cases.

Fluorophores will rarely be attached to an amino acid directly, but will instead be attached via a linker. The choice of linker can also have an effect on the way the labelled SSB functions, as the size, shape and flexibility of the linker can change the ability of a linker to come into proximity with other groups.

Labels are preferably attached to the SSB in a manner that does not introduce a new chiral centre. Thus the label-protein adduct does not exist in diastereoisomeric form thus allowing a substantially homogenous labelled SSB to be obtained. This can be achieved by the use of linkers such as the haloacetamides (preferably iodoacetamides).

When using labels such as rhodamines it is also preferable to minimise any non-covalently bound rhodamine since this is likely to have high fluorescence and increase the background levels. Experimental conditions must thus be chosen appropriately as described below.

After attachment of the label, labelled protein will usually be purified to separate it from free label and from any mis-labelled protein. The mis-labelled protein may be unlabelled protein with which label did not react or protein where label has attached in the wrong position (either in place of or in addition to the desired label). During purification of the labelled protein, treatment with a thiol reagent may be included, such as β-mercaptoethanol, dithiothreitol or sodium 2-mercaptoethanesulfonate as this can improve the fluorescence response of the protein.

Where more than one label can be attached, it is preferred to use the protein in homogenous form. A homogenous form, e.g. pure double-labelled species, may be purified (for example by ion exchange and/or hydrophobic interaction chromatography) to obtain homogenous, double-labelled species. Single and double labelled SSBs can be distinguished by methods such as electrospray mass spectrometry.

The detectable label preferably shows an increase in its detectable characteristics upon binding single stranded DNA. Advantageously, this is at least 4-fold, more preferably 5-fold and most preferably 6-fold or greater.

Assay Methods

The labelled SSBs of the invention can be used in assays for general biochemical use for detecting single stranded DNA in a sample. For example, in detecting strand separation of double stranded DNA which is catalyzed by helicases and allows further processing such as repair and replication. Alternatively the labelled SSBs of the invention can be used in assays to measure the removal of single stranded DNA, or in assays to measure the decrease in double stranded DNA. These assays can be qualitative or quantitative. The invention is particularly useful for following the kinetics of reactions, because of the rapid reaction time of the SSBs. The assays can be used in screening methods for inhibitors of DNA processing enzymes. Such assays comprise assaying single stranded DNA levels in vitro using a SSB according to the present invention in the presence and absence of the inhibitors and assaying for an alteration in the single stranded DNA levels.

The single stranded DNA may be a single strand of DNA or may be a single stranded region of a DNA duplex.

The sample may be from any source, including serum, urine, saliva, sweat, tissue culture, cell extracts, cell lines, food, beverages, pharmaceuticals and environmental (for example water). If concentrations of single stranded DNA in the sample are high, samples may be diluted as necessary to achieve accurate quantification of single stranded DNA levels.

The kinetics of these methods may depend on salt concentration or the presence of a particular anion. A skilled person would be able to select the appropriate conditions to carry out the methods of the invention.

These methods will typically be in vitro assays.

Thus the invention provides a method for detecting single stranded DNA in a sample comprising the steps of:
  (i) mixing the sample with the modified SSB comprising at least one detectable label; and
  (ii) detecting a change in the mixture arising from the interaction between the single stranded DNA and the SSB.

The change detected in (ii) can be related to the concentration of single stranded DNA in the sample.

By employing this method, using a modified SSB, it is possible to follow the kinetics of biological systems due to the extremely rapid reaction time of the method.

The invention also provides a modified SSB of the invention, for use in an assay of single stranded DNA.

A further aspect of the invention provides a polypeptide sequence of SEQ ID NO: 1 in which one or more wild type amino acid residues are changed to a cysteine residue. The invention further provides a polypeptide sequence of SEQ ID NO: 2, SEQ ID NO: 3 or SEQ ID NO: 4. The invention further provides the nucleotide sequences which encode the polypeptide sequences of SEQ ID NO: 1, SEQ ID NO: 2, SEQ ID NO: 3 and SEQ ID NO: 4.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x+10%.

BRIEF DESCRIPTION OF DRAWINGS

FIG. 1 shows the fluorescence spectra and titration of IDCC-*E. coli* SSB with $dT_{70}$ (SEQ ID NO: 5). Measurement conditions were as in Table 1.

FIG. 2 shows the association kinetics of IDCC-*E. coli* SSB with $dT_{70}$. 5 nM IDCC~*E. coli* SSB was mixed with various concentrations of $dT_{70}$ and fluorescence intensity followed with time in a stopped flow apparatus. Conditions were as in Table 1, except measurements were at 25° C.

FIG. 6 shows absorbance and fluorescence spectra and titration of rhodamine-*E. coli* SSB with $dT_{70}$.

FIG. 8 shows an alignment of seven SSB sequences from *Escherichia coli* (SEQ ID NO: 1), Enterobacteria phage P1 (SEQ ID NO: 7), *salmonella typhimurium* (SEQ ID NO: 8), *bacillus licheniformis* (SEQ ID NO: 9), *campylobacter jejuni* (SEQ ID NO: 10), *pseudomonas syringae* (SEQ ID NO: 11) and *listeria innocua* (SEQ ID NO: 12).

FIG. 9 shows an assay in which IDCC-SSB is used to monitor helicase activity of PcrA and RecBCD.

FIG. 10a shows an IDCC-SSB assay, at high and low ionic strength and 37° C. The control shown is at low ionic strength in the absence of ATP. FIG. 10b shows an IDCC-SSB assay as in FIG. 10a, but with 50 nM (in nucleotides) pBR322. FIG. 10c shows a dye displacement assay. Experimental conditions were the same as in FIG. 10a, but the IDCC-SSB was replaced with wild type SSB and the buffer was supplemented with 200 nM Hoechst 33258 dye. The fluorescence signals were calibrated using heat-denatured EcoRI-linearized pBR322 under identical solution conditions (both high and low salt) and instrument settings.

MODES FOR CARRYING OUT THE INVENTION

Figure 1A:
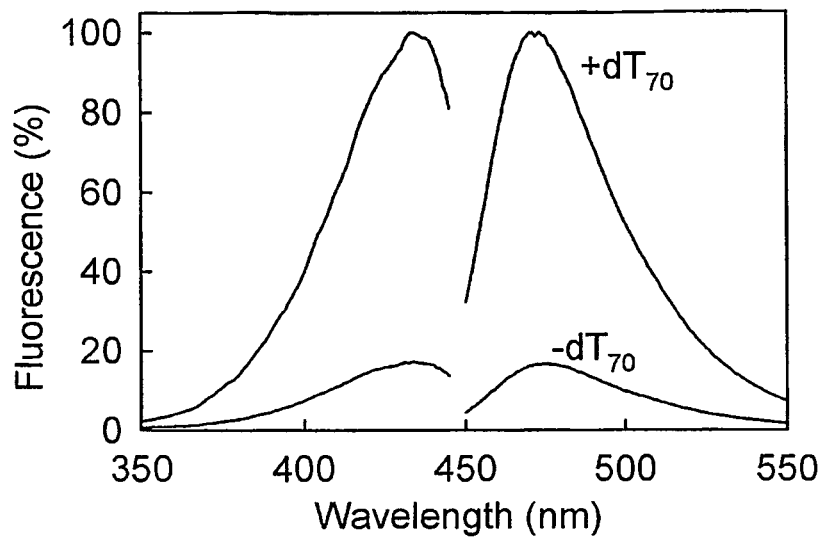
FIG. 1A shows the excitation and emission spectra, in the presence and absence of 580 nM $dT_{70}$. Excitation was at 433 nm, emission at 476 nm.

Preparation of mutant *E. coli* SSB proteins

The wild type *E. coli* ssb gene was cloned into a pET15b vector using PCR with primers containing flanking NdeI and BamHI restrictions sites. This vector was used as a template for site directed mutagenesis to produce genes for G26C, S92C or W88C *E. coli* SSB. The pET15b constructs were sequenced to confirm the presence of the desired mutations and the integrity of the remainder of the ssb gene. The mutated genes were then transferred to pET22b vectors using the NdeI and BamHI restriction sites and these were used to transform BL21 pLysS for overexpression using the T7 promoter system. Cells were grown in 2l of LB at 37° C. to mid-log phase and expression was induced with 1 mM IPTG. After three hours, the cells were harvested, resuspended in 50 ml of 50 mM Tris.HCl pH 7.5, 200 mM NaCl, 1 mM EDTA, 1 mM dithiothreitol and 10% sucrose, and stored at −80° C.

The mutant *E. coli* SSB proteins were purified at 4° C. using a modification of the method of Lohman et al. [14]. The cell suspension was thawed and 0.1 mM PMSF added. Cell lysis by sonication was followed by centrifugation. The supernatant was collected and polymin P (10% stock solution, pH 6.9) was added slowly to 0.4%, followed by constant stirring for 15 min. A pellet was collected by centrifugation at 10,000 rpm for 20 min and then completely resuspended in 50 ml of 50 mM Tris.HCl pH 8.3, 20% glycerol, 1 mM EDTA and 0.4 M NaCl using a Dounce homogenizer, followed by stirring for 30 min. Insoluble material was removed by centrifugation at 10K for 20 min. Solid ammonium sulfate was added to the supernatant very slowly to 150 g l$^{-1}$. After stirring for 30 min, a pellet was collected by centrifugation at 13K for 30 min. The pellet was resuspended in 50 nil of 50 mM Tris.HCl pH 8.3, 20% glycerol, 1 mM EDTA and 0.2 M NaCl. The resuspension was centrifuged at 18K for 20 min and passed through a 0.2 µm syringe filter. A 5 ml Hi-Trap heparin column was equilibrated in 50 mM Tris.HCl pH 8.3, 20% glycerol, 1 mM EDTA. The sample was loaded at a low salt concentration by mixing with equilibration buffer (in the ratio 16:84 for sample to buffer volume) immediately before the column in the mixing chamber of the chromatography apparatus. This is necessary because *E. coli* SSB is prone to precipitation, if kept for extended periods at the low salt concentration required for binding to heparin. The column was then washed with equilibration buffer and *E. coli* SSB was eluted with a 150 ml gradient from 0 to 1 M NaCl in this buffer. Peak fractions were pooled, dialyzed extensively against storage buffer (20 mM Tris.HCl pH 8.3, 1 mM EDTA, 0.5 M NaCl, 50% glycerol and 1 mM β-mercaptoethanol), and stored at −80° C. Protein concentration was determined by measuring absorbance at 280 nm using a theoretical extinction coefficient of 27880 $M^{-1}cm^{-1}$ for the monomer. Concentrations given herein are those of the monomer, unless otherwise stated.

Labelling Mutant SSB Proteins

Cysteine mutants of *E. coli* SSB were covalently modified with a variety of fluorescent dyes.

The following protocol is used for labeling G26C *E. coli* SSB with the diethylaminocoumarin iodoacetamide, IDCC. An aliquot of *E. coli* SSB (G26C) (5 mg in 1.3 ml) was incubated with dithiothreitol (DTT) for 10 min in 20 mM Tris.HCl pH 7.5, 1 mM EDTA, 500 mM NaCl, 20% glycerol. The protein had DTT removed using a PD10 column, pre-equilibrated in the same buffer that had been degassed by bubbling nitrogen. IDCC in four-fold excess over the ~100 μM protein was added and incubated under nitrogen for 2 h at room temperature with end-over-end stirring and protection from light. Excess IDCC was removed by reaction with sodium 2-mercaptoethane sulfate (10-fold excess over protein) for 10 min. The incubation mixture was filtered through a membrane (0.2 μm pores, polyethersulfone). The protein was isolated by passing through a P4 gel filtration column (1×30 cm), pre-equilibrated in 20 mM Tris.HCl pH 8.3, 1 mM EDTA, 500 mM NaCl, 20% glycerol. The protein concentration was calculated from the coumarin absorbance at 430 nm, where the extinction coefficient is 44800 $M^{-1} cm^{-1}$, assuming it is the same as IDCC, [17]. Glycerol was added to the labeled protein (IDCC-SSB), which was then stored at −80° C.

The following protocol is used for labeling W88C *E. coli* SSB with the 6-IATR. An aliquot of *E. coli* SSB (W88C) (5 mg) in storage buffer (0.4 ml) was incubated with 5 mM DTT for 10 min and then applied to a PD10 gel filtration column, pre-equilibrated in 20 mM Tris HCl pH 8.3, 1 mM EDTA, 500 mM NaCl, 20% Glycerol. The protein was eluted with the same buffer, resulting in 1.5 ml of 93 μM *E. coli* SSB. 6-IATR was added to 372 μM and the solution was capped under nitrogen, protected from light, and mixed end-over-end for 90 mM at room temperature. Sodium mercaptoethyl sulfonate (931 μM) was added to remove excess 6-IATR and the solution was incubated for 10 min. The incubation mixture was filtered through a membrane (0.2 μm pores, polyethersulfone). The protein was isolated by passing through a P4 gel filtration column (1×30 cm), pre-equilibrated in 20 mM Tris.HCl pH 8.3, 1 mM EDTA, 500 mM NaCl, 20% glycerol. The protein concentration was calculated assuming an extinction coefficient of 52 $mM^{-1} cm^{-1}$ at 534 nm (see below). Glycerol was added to make it 50% (v/v) and the protein (6-IATR-SSB) was stored in aliquots at −80° C.

In practice labeling on amines can also occur, when using thiol-selective reagents. Mass spectrometry of the rhodamine labeled *E. coli* SSB showed that ~90% of the protein was the desired product, singly labeled *E. coli* SSB, together with small amounts of unlabeled and doubly labeled protein. The labeling conditions described minimize these side products. In addition it is important to try to minimise any non-covalently bound rhodamine since this is likely to have high fluorescence and so increase the background. Gel filtration after the labeling seemed effective in this: further purification on a heparin column resulted in only a slight increase in fluorescence enhancement on DNA binding.

The molecular masses of unlabeled and labeled proteins were determined by electrospray mass spectrometry as described previously [4].

Other dyes and mutant *E. coli* SSB were labeled similarly to the methods described above with some variation in length of time or concentrations of protein and dye.

Absorbance and Fluorescence Measurements.

Absorbance spectra were obtained on a Beckman DU640 spectrophotometer. Fluorescence measurements were obtained on a Cary Eclipse fluorimeter with a xenon lamp, using 3 mm-path length cells. Quantum yields were measured at 20° C. in 1 cm-path length cells using solutions with absorbance of ~0.03 $cm^{-1}$ at the exciting wavelength. The corrected emission spectra were obtained from 435 to 600 nm. The quantum yields for IDCC-*E. coli* SSB were measured relative to Coumarin 343 which has a known value of 0.63 [18].

Stopped-flow experiments were carried out on a HiTech SF61MX apparatus, with a mercury-xenon lamp and HiTech IS-2 software. There was a monochromator and 4 mm slits on the excitation light and an appropriate cut-off filter on the emission (436 nm excitation and 455 nm filter for IDCC-*E. coli* SSB). In measurements described here, the stated concentrations are those in the mixing chamber, unless shown otherwise. Data were fitted to theoretical curves using either the HiTech software or Grafit 5 [19].

Specificity Tests

Lambda DNA was heat denatured by heating the following solution for 5 min at 95° C.: 261 μM DNA (in terms of nucleotides), 50 mM Tris.HCl pH 7.5, 10 (v/v) sucrose, 2 mM magnesium acetate, 2 mM DTT. The product was put on ice and used immediately. ssRNA (as a ladder of seven lengths) was heat denatured and used in the same way. The nucleic acids were tested with IDCC-*E. coli* SSB by adding 23 nM (in terms of nucleotides) to 400 nM IDCC-*E. coli* SSB at 30° C. in 25 mM Tris.HCl pH 7.5, 200 mM NaCl, 1 mM DTT, and 5 μM bovine serum albumin. Excitation was at 430 nm, emission at 475 nm.

Helicase Assays

All experiments were performed at 37° C. All data presented are representative single trace measurements with no averaging. For measurements of PcrA helicase activity, experiments were performed by pre-incubating 25 nM PcrA and 4 nM RepD (monomer) with 1 nM pCERoriD DNA substrate (6.2 μM nucleotides) in a buffer containing 50 mM Tris.HCl pH 7.5, 10 mM $MgCl_2$, 100 mM KCl and 1.1 μM IDCC-SSB (monomer) for 5 min. The reaction was initiated by rapid mixing with an equal volume of 0.5 mM ATP in the same buffer. The protocol for this experiment is essentially identical to that performed previously [20], except that the wild-type *Bacillus subtilis* SSB has been directly replaced with IDCC-SSB. For measurements of RecBCD helicase-nuclease activity, experiments were performed by pre-incubating 5 nM (saturating) RecBCD with 1 nM ClaI-linearised pADGF0 DNA (6.1 μM nucleotides) in a buffer containing 25 mM Tris-acetate pH 7.5, 2 mM magnesium acetate, 1 mM DTT and 1.1 μM IDCC-SSB (monomer) for 5 minutes. The reaction was initiated by rapid mixing with 1 mM ATP in the same buffer. The fluorescence signals were calibrated using heat-denatured Lambda DNA under identical solution conditions and instrument settings. For the measurements of AddAB activity, experiments were performed by pre-incubating 2.5 nM AddA$^{D1172A}$B$^{D961A}$ [21,22] with 0.1 nM (870 nM nucleotides) EcoRI-linearized pBR322 DNA (unless stated otherwise), in a buffer containing 25 mM Tris.HCl pH 7.5, 2 mM MgCl$_2$, 175 nM IDCC-SSB (monomer) and either 20 mM (low ionic strength) or 200 mM (high ionic strength) NaCl for 5 min. The reaction was initiated by rapid mixing with an equal volume of 0.5 mM ATP in the same buffer. For the dye displacement assay, the IDCC-SSB was replaced with wild type SSB and the buffer was supplemented with 200 nM Hoechst 33258 dye. The fluorescence signals were calibrated using heat-denatured EcoRI-linearized pBR322 under identical solution conditions (both high and low salt) and instrument settings. Calibration with heat-denatured Lambda DNA produced virtually identical results. For all experiments, the unwinding data are plotted in arbitrary fluorescence units and as apparent nanomolar ssDNA (in nucleotides), based on the calibrations. It should be noted that the measurement is of SSB binding, rather than of ssDNA per se, and that these values may differ if ssDNA is produced in a form that cannot be bound by the SSB protein (for example, if there is extensive nuclease activity).

Coumarin-*E. coli* SSB Mutants (S92C and G26C) Results

The crystal structures of *E. coli* SSB suggest there are only minor changes in protein subunit conformation on association with DNA [12, 13]. In wrapping around the surface of the tetramer, DNA winds through a series of channels in the protein surface. Two sites for labeling with fluorophores were chosen on loops that are at the top of such channels and single cysteines were introduced into the protein to provide these sites. One mutation (S92C) is in a loop that is essentially unaltered between the bound and unbound structures. Another mutation (G26C) is at the lip of a channel and in a loop that may be flexible in the DNA-free structure, but is well defined in the DNA-bound form. In either case, the wrapping of DNA around the *E. coli* SSB surface provides significant opportunity for changes in fluorophore environment. Mainly fluorophores whose intensity changes with environment were chosen with these two mutant *E. coli* SSBs.

Table 1 shows the fluorescence intensity changes for these two mutant *E. coli* SSBs. In order to obtain a molecule suitable for solution measurements, a suitably large fluorescence increase on binding DNA, together with reasonably bright fluorescence quantum yield are the main criteria. Fluorescence spectra of 250 nM labeled *E. coli* SSB (tetramer concentration) were measured at 30° C. in 25 mM Tris.HCl pH 7.5, 200 mM NaCl, 1 mM DTT, and 5 µM bovine serum albumin.

Excitation was at the appropriate wavelength for the fluorophore and the emission intensities at the maximum were measured in the absence and presence of saturating dT$_{70}$. The two coumarins, IDCC and MDCC gave the largest fluorescence enhancement with G26C and this mutant protein labeled with IDCC, IDCC-*E. coli* SSB, was chosen for further study for two reasons. Firstly it gave consistently a larger increase than MDCC. Secondly, it does not have the potential complications of forming a chiral center on reaction with a thiol. In the case of MDCC, reaction of its maleimide with a protein cysteine causes the production of diastereoisomers. When this phenomenon was observed with a similar sensor for phosphate, it was shown that the two diastereoisomers have different fluorescence properties [4]. In contrast, reaction of IDCC with a thiol should produce only a single molecular species.

TABLE 1

Fluorescence changes for a survey of various mutant *E. coli* SSB: dye combinations.

| Fluorescent label | Fluorescence ratio (+/− dT$_{70}$) | |
| --- | --- | --- |
| | S92C | G26C |
| IDCC | 2.8 | 6.1 |
| MDCC | 2.2 | 4.9 |
| MIANS | 0.4 | — |
| 6-IATR | 1.3 | 2.8 |
| Alexa Fluor 488 | 3.1 | 3.3 |
| Alexa Fluor 546 | 1.5 | 2.3 |

Figure 1B:
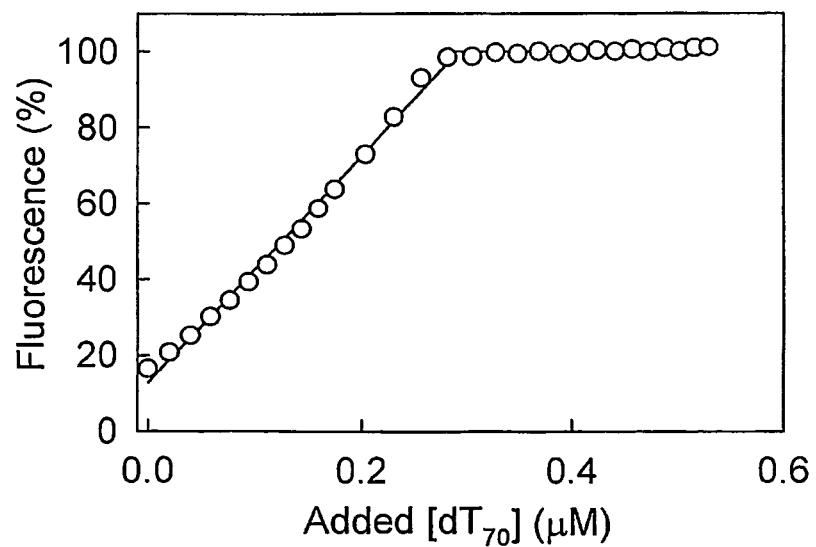
FIG. 1B shows the titration of emission intensity (excitation at 430 nm, emission 475 nm) as a function of $dT_{70}$. The lines are the best linear fit up to 0.28 µM $dT_{70}$, and the best fit horizontal line for remaining points.

FIG. 1 shows the change in fluorescence spectra when IDCC-*E. coli* SSB binds DNA. The change was similar when poly-dT was used (poly-dT consists of poly (dT) strands of various lengths, each length being approximately a few hundred bases). Fluorescence enhancements of ~6-fold could be obtained. A titration of DNA into a solution of IDCC-*E. coli* SSB shows a fairly linear increase in fluorescence, followed by a sharp break as the maximum fluorescence is maintained. This is consistent with very tight binding of DNA with the *E. coli* SSB. The slight curve in the titration at low DNA suggests that a small amount of unlabeled *E. coli* SSB is present and this binds the DNA more tightly. In this preparation, mass spectra suggest ~0.5-10% of the *E. coli* SSB is unlabeled. Other dye-*E. coli* SSB combinations also showed such curvature.

The fluorescence quantum yield of IDCC-*E. coli* SSB was measured to assess how fluorescent the probe is in absolute terms in the absence of DNA. The quantum yield is 0.029 and 0.15 in the presence of saturating dT$_{70}$. Note that the quantum yield reflects the integrated area of the emission spectrum, rather than the intensity at a particular wavelength. In comparison, the diethylaminocoumarin attached to a small molecule and therefore presumably having the medium environment only, has a quantum yield of 0.01 to 0.04 [4], [23]. This suggests that in the absence of DNA, the coumarin's fluorescence is largely unaffected by the protein.

Figure 2A:
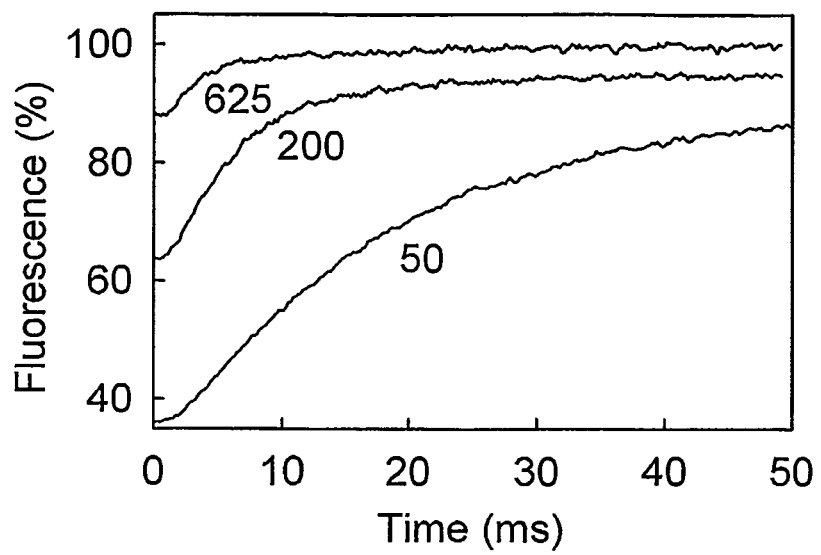
FIG. 2A shows typical individual traces at nanomolar concentrations of $dT_{70}$. Traces were normalized to finish at 100% and offset by 5% from each other. The fast traces have diminished amplitude, mainly due to loss of signal during the dead time of the instrument (~2 ms).
Figure 2B:
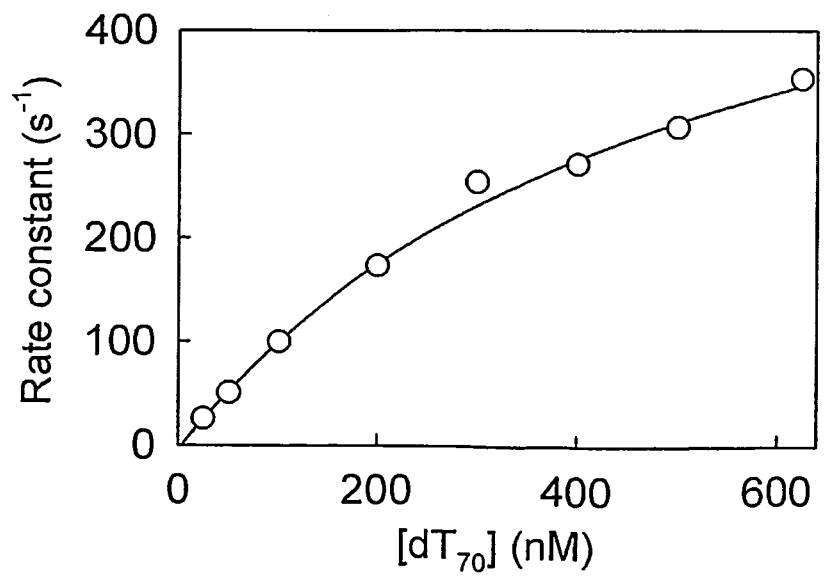
FIG. 2B shows the dependence of rate on concentration of DNA. Each trace was fitted to a single exponential. Data shown are the averages of typically 3 traces from each of two separate experiments. All the rate constants from individual traces were fit to a hyperbola, as described below.

In order to assess the applicability of IDCC-*E. coli* SSB as a probe for kinetic assays, it is important to know the feasible rates of DNA binding and dissociation. Association kinetics were measured in pseudo-first order conditions with a large excess of dT$_{70}$ over IDCC-*E. coli* SSB (FIG. 2). Individual fluorescence traces fitted single exponentials well and the rate increased with DNA concentration. The DNA concentration dependence suggested that the relationship may be hyperbolic and this was fitted to the data. Such dependence is consistent with a two-step binding mechanism:

$$\text{SSB} + \text{DNA} \underset{}{\overset{1}{\rightleftharpoons}} \text{SSB·DNA} \underset{}{\overset{2}{\rightleftharpoons}} \text{SSB*·DNA} \tag{1}$$

In this case, the fit gives 1/K$_1$=518 nM and k$_{+2}$=642 s$^{-1}$. The intercept with the ordinate is not significantly different from zero and so does not give an accurate measure of the dissociation rate. Possible implications of this two-step mechanism are described below.

Figure 3:
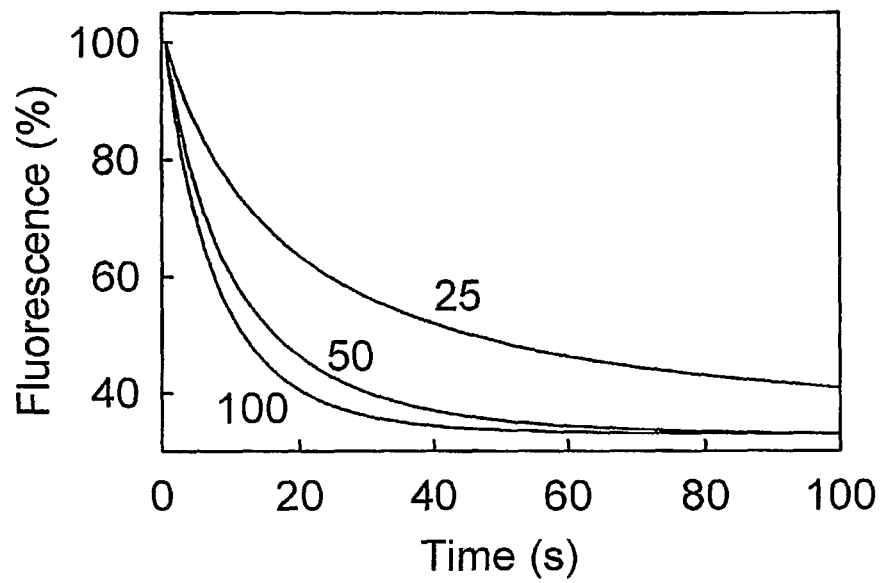
FIG. 3 shows the dissociation kinetics of IDCC-*E. coli* SSB 5 nM of this complex was mixed with a large excess of unlabeled *E. coli* SSB as a trap. S92C *E. coli* SSB was used at the concentration shown. Experimental conditions were as in FIG. 2.

The dissociation kinetics were measured directly by displacing IDCC-*E. coli* SSB from its complex with dT$_{70}$ by unlabeled *E. coli* SSB (FIG. 3). The aim in this type of measurement is to get conditions where the observed rate is solely determined by dissociation of the complex. Use of a large excess of the trap, in this case unlabeled *E. coli* SSB, normally achieves this. A test is to vary the trap concentration: a constant rate is consistent with the dissociation being rate limiting. In this case, the observed traces varied with concentration of unlabeled *E. coli* SSB and the traces were not good fits to single exponentials. However, the traces suggest that the observed rates are ~0.1 s$^{-1}$. Possible reasons for the complex traces are given below in terms of wrapping the DNA around the *E. coli* SSB.

Figure 4:
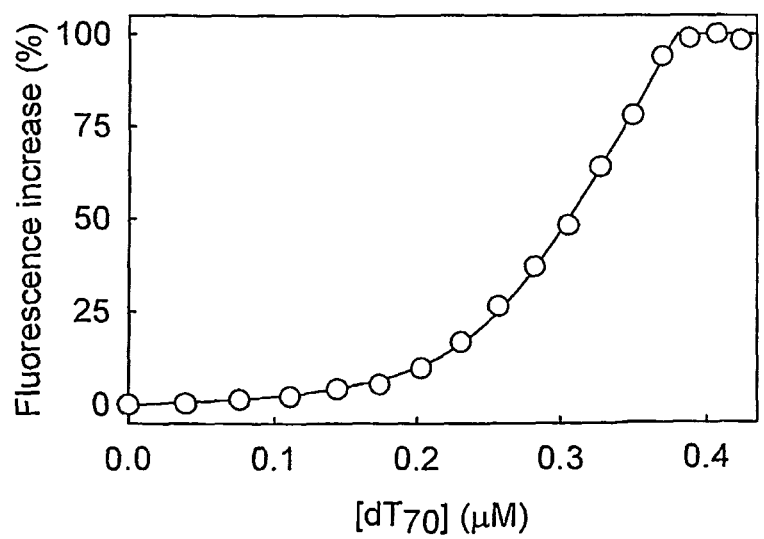
FIG. 4 shows a competition titration of $dT_{70}$ into a mixture of unlabeled *E. coli* SSB (S92C) and IDCC-*E. coli* SSB. Otherwise conditions are as in FIG. 1. The data were fitted to the equation for competing equilibria of the following species: *E. coli* SSB, *E. coli* SSB IDCC-*E. coli* SSB and IDCC-*E. coli* SSB.$dT_{70}$ and assumed tight binding, so essentially there was no free DNA until in excess over the two *E. coli* SSB species. The ordinate is the extent of formation of MCC-*E. coli* SSB-$dT_{70}$, as measured by the fluorescence. The line shows the best fit with 0.13 µM IDCC-*E. coli* SSB, 0.25 µM *E. coli* SSB (tetramer concentrations) and the ratio of $K_d$(IDCC-*E. coli* SSB)/$K_d$(*E. coli* SSB) is 28.

In order to determine the effect of labeling on the affinity of *E. coli* SSB for ssDNA, dT$_{70}$ was titrated into a mixture of unlabeled *E. coli* SSB and IDCC-*E. coli* SSB (FIG. 4). It is apparent that low concentrations of DNA bind mainly to the unlabeled *E. coli* SSB, as there is only a small increase in fluorescence. This implies that the unlabeled protein has the higher affinity. Fitting the data to competing binding equilibria, as described in the figure legend, suggests that the ratio of the dissociation constants is 28. In order to show that this change in affinity is not specific to the coumarin label, the measurement was repeated with the 6-IATR-labeled G26C SSB and this gave a similar result.

The specificity of the response was measured for other nucleic acid species, as described above. Lambda dsDNA gave no response, but after heat treatment gave the full fluorescence increase. ssRNA (before or after heat treatment) gave no response. These data suggest that IDCC-*E. coli* SSB is specific for ssDNA.

Figure 5:
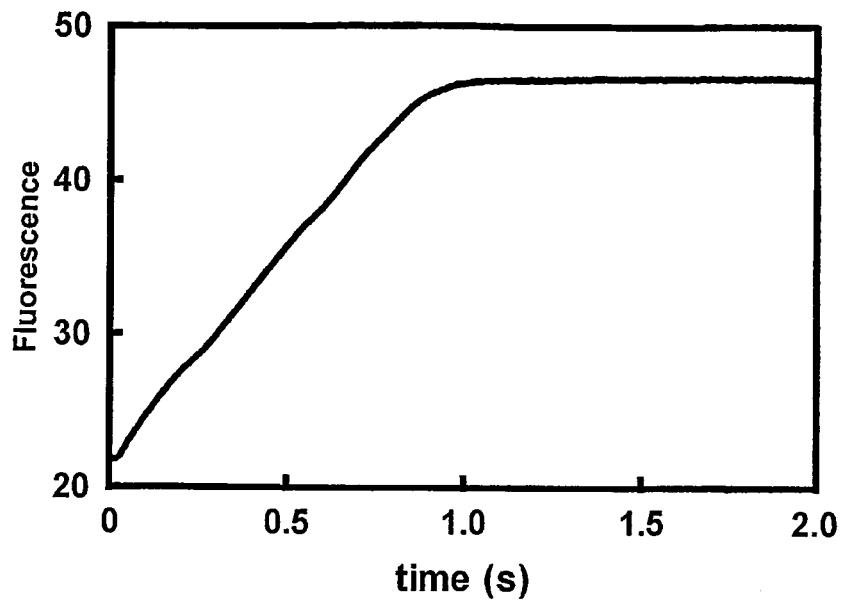
FIG. 5 shows an assay of unwinding dsDNA, using helicase RecBCD 1 nM linearized plasmid DNA (pADGFO_ClaI—3 kb) was mixed in a stopped-flow apparatus with excess RecBCD in the presence of ATP and 500 nM IDCC-*E. coli* SSB.

The IDCC-*E. coli* SSB reagentless sensor can be applied to helicase assays for unwinding dsDNA. An example is given in FIG. 5, a measurement of RecBCD unwinding a 3 kb length of dsDNA. Under the conditions used, RecBCD has high processivity and will unwind all of the DNA [24]. The increase in fluorescence is linear until the entire length of DNA is unwound. Because the helicase binds to blunt ends, under the conditions here RecBCD unwinds from each end of the linear DNA at ~1500 bases per second, similar to that measured using a dye displacement assay [24].

Figure 9A:
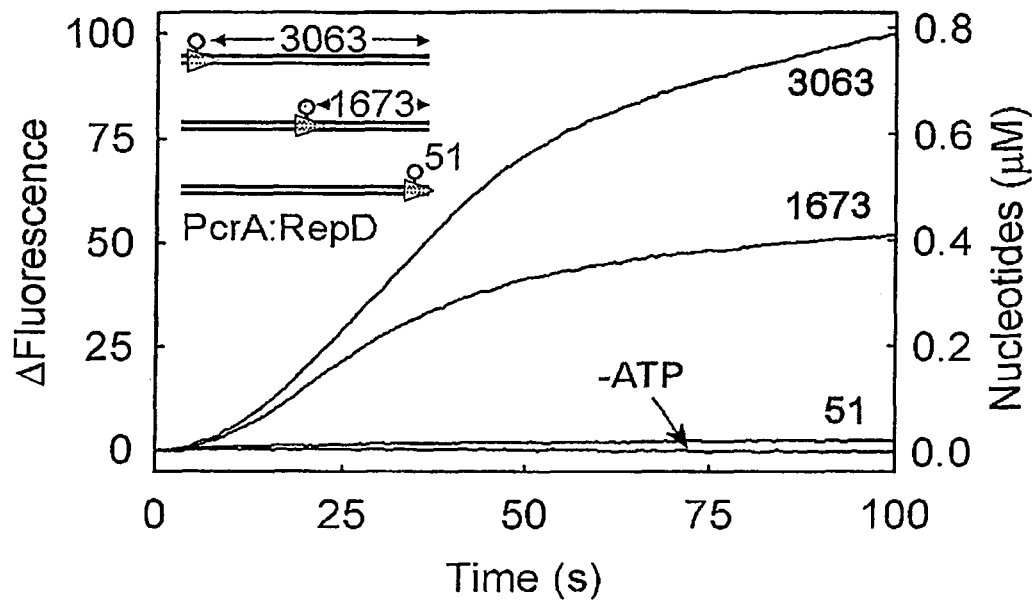
FIG. 9a shows the unwinding of three different lengths of DNA substrates, catalyzed by PcrA/RepD, monitored using IDCC-SSB fluorescence. The schematic shows the linearized plasmid DNA: RepD initiator protein loads PcrA at oriD sites, and the helicase processively unwinds the duplex to the right of oriD. The distance (in base pairs) between the oriD and the end of the DNA is indicated. The "-ATP" control was on the longest DNA.
Figure 9B:
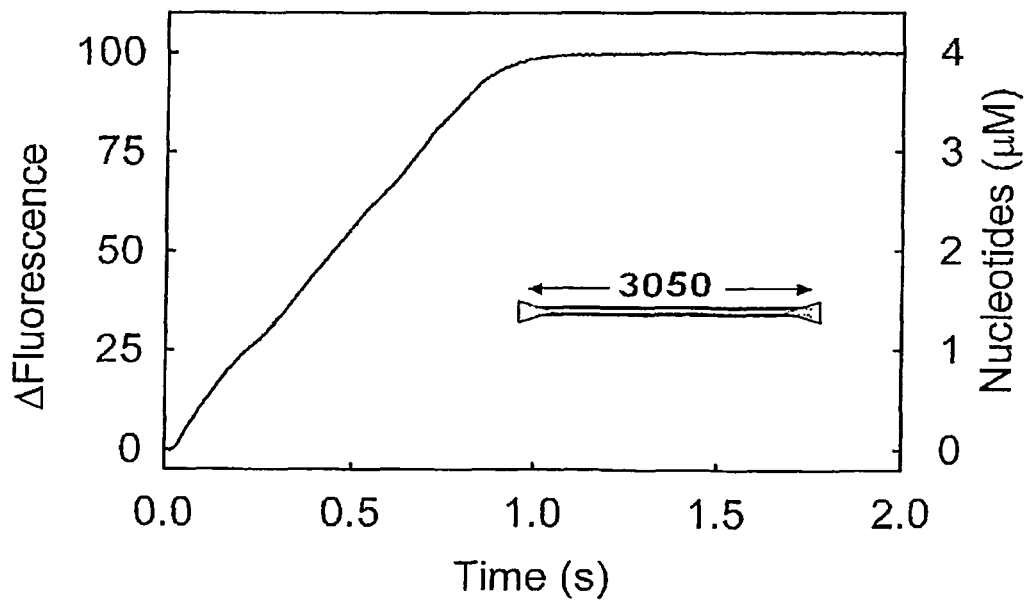
FIG. 9b shows linearized pADGF0 unwinding by saturating RecBCD, monitored using IDCC-SSB fluorescence. The schematic shows the pADGF0 plasmid with the length of the DNA indicated.

RecBCD is involved in the recombinational repair of DNA breaks and initiates unwinding from DNA ends. RecBCD is the fastest and most processive helicase reported in the literature [25, 26, 1]. DNA unwinding by the RecBCD helicase-nuclease was again monitored. Following addition of ATP to pre-formed RecBCD.DNA complexes, there is a rapid linear fluorescence increase followed by a sharp breakpoint that marks the end of the unwinding reaction after about 0.9 seconds. This suggests an unwinding rate of ~1700 bp s$^{-1}$ per RecBCD binding site (FIG. 9b), in excellent agreement with previous estimates [27].

Further assays were carried out to demonstrate the use of the MCC-SSB reagentless biosensor to monitor DNA unwinding catalyzed by DNA helicases. IDCC-SSB was employed at concentrations well above the measured K$_a$ and at a stoichiometry of approximately 1 MCC-SSB monomer per 5 nucleotides substrate DNA, to ensure a linear fluorescence response regardless of SSB binding mode (see discussion). In one example (FIG. 9a) three different lengths of dsDNA substrates are unwound by PcrA helicase, after nicking by RepD at the oriD origin [28,29]. In each case, the dsDNA has the oriD site at a different position relative to one end. Unwinding by PcrA starting from oriD is unidirectional, and so each substrate is unwound to different extents by the helicase. The rates and extent of reactions are in good agreement with those determined under identical conditions using tryptophan fluorescence [20]. However, the data are of much higher quality: averaging of multiple traces and significant corrections for photobleaching are avoided when using extrinsic MCC fluorescence. Moreover, the use of IDCC-SSB will allow facile analysis of the effect of PcrA and RepD concentrations on the observed unwinding, which had previously been limited by the background fluorescence from these components.

Figure 10:
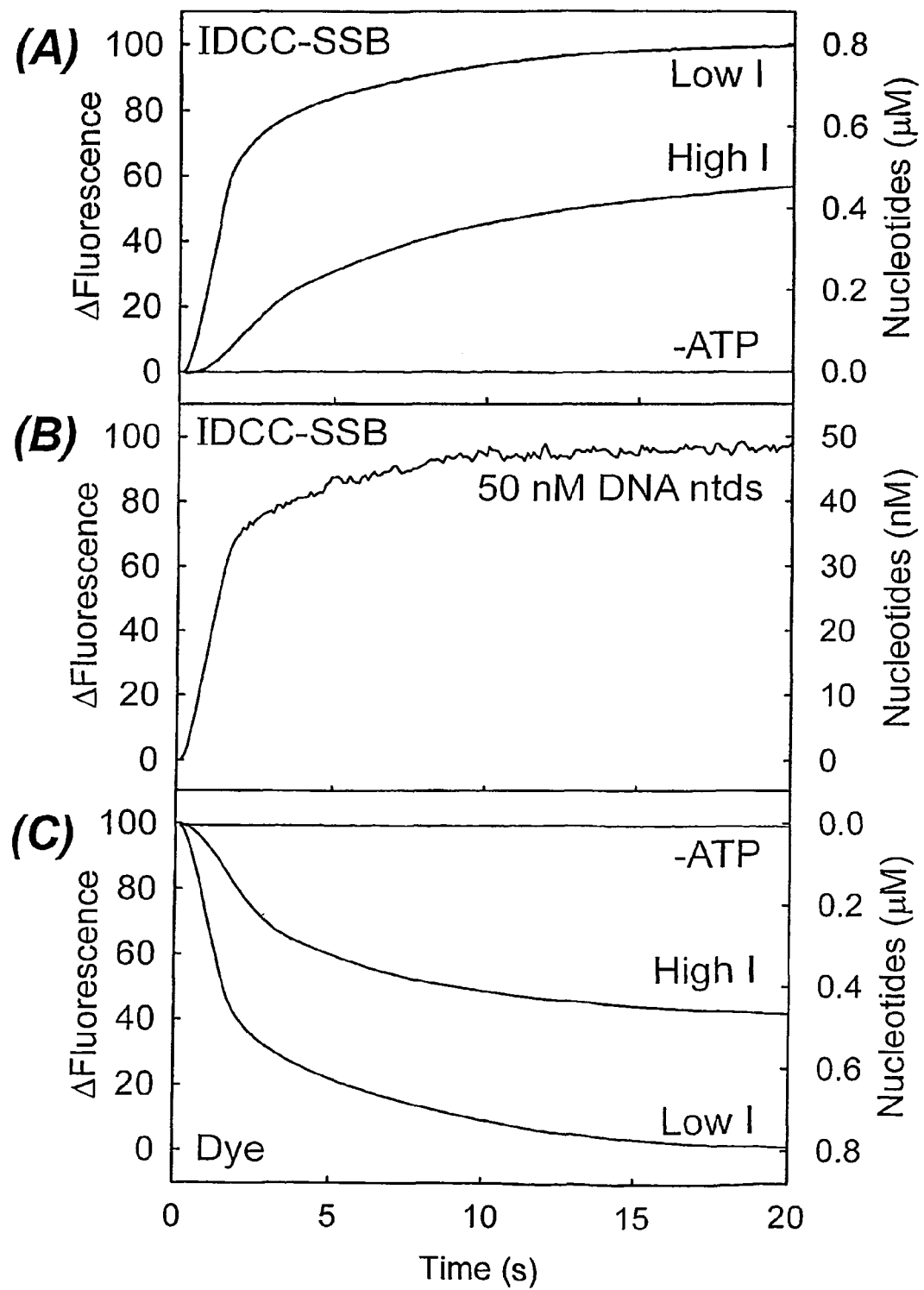
FIG. 10 shows a comparison of IDCC-SSB and dye displacement assays for the helicase AddAB. Experiments were performed as described in the Experimental Procedures.

In a further example, the unwinding of linearized plasmid DNA by a nuclease-deficient mutant of the *B. subtilis* AddAB helicase-nuclease was analysed (FIG. 10). AddAB is a functional analogue of RecBCD that is also involved in the processing of DNA breaks for recombinational repair. It binds tightly to free DNA ends and, in the presence of ATP, translocates and unwinds DNA rapidly and processively [30]. The data from the IDCC-SSB sensor was compared directly with those from dye-displacement assays [1] at both low and high ionic strength. At low ionic strength, AddAB unwinds >90% of the DNA substrate at a maximum observed rate of 400 nM ntds (equivalent to ~1000 bp s$^{-1}$ per AddAB binding site). As would be expected for a DNA-binding protein, AddAB-catalyzed DNA unwinding is less effective at high ionic strength, and both the extent and the maximum observed rate (85 nM ntds s$^{-4}$) of the reaction are diminished. Importantly however, the dye displacement assay produces similar traces to those obtained using IDCC-SSB regardless of the ionic strength; the maximum observed rates are 340 and 110 nM ntds s$^{-1}$ respectively. As expected, the observed unwinding amplitude was proportional to the DNA substrate concentration and a single trace measurement for 50 nM (in nucleotides) substrate DNA retained excellent signal to noise ratio (FIG. 10b).

Discussion

The characterization of *E. coli* SSB labeled with a single fluorophore per subunit is described for use as a reagentless biosensor for ssDNA. Although several different types of fluorophore were tested, the best signal properties were obtained with a diethylaminocoumarin derivative, IDCC. When bound to the cysteine of the G26C *E. coli* SSB, the fluorescence quantum yield is similar to that of the coumarin in a small molecule in aqueous medium. On binding DNA to the *E. coli* SSB, there is a large increase in fluorescence intensity, but essentially no change in absorbance of the coumarin.

Competition experiments with unlabeled *E. coli* SSB suggest that the latter binds ssDNA ~20-fold more tightly than does IDCC-*E. coli* SSB. Even so, the labeled protein still binds DNA very tightly and seems to lack dsDNA binding in the high salt conditions used in this study. It was possible to do a titration of dT$_{70}$ into 2.5 nM IDCC-*E. coli* SSB tetramers. The shape of the fluorescence response was similar to that in FIG. 1, so that the K$_d$<<2.5 nM, but it was not possible to get an estimate of the value. The kinetics of association and dissociation were modeled using a two-step mechanism. From this, step 1 has an equilibrium constant (1/K$_1$) of 518 nM. As k$_{+2}$=642 s$^{-1}$ and k$_2$~0.1 s$^{-1}$, the overall dissociation constant is ~80 pM.

Previous work on the kinetics [15] was able to distinguish three steps in the binding mechanism, by obtaining data at microsecond resolution using relaxation techniques. The steps were interpreted in terms of wrapping the DNA around the tetramer. Another study [31] using, in particular, DNA labeled with fluorophores and stopped-flow methods (and so millisecond times), had a two-step binding mechanism with the first step likely to be diffusion controlled. In the present measurements, the slope of the tangent to the hyperbola in FIG. 2B at low DNA concentration is k$_{+2}$K$_1$ in terms of the mechanism in Equation 1, assuming step 1 is fast relative to step 2. This slope is ~10$^9$ M$^{-1}$s$^{-1}$, also suggesting binding may be controlled by diffusion. The previous studies estimated the dissociation rate constant as 0.044 s$^{-1}$ at 25° C. and 200 mM NaCl, likely to be consistent with the value obtained here. They also showed that the kinetics are very dependent on salt concentration and on whether chloride or bromide is the anion.

At the concentrations used in the measurement of dissociation kinetics, any dissociated DNA should bind to the trap, unlabeled *E. coli* SSB at ~25 s$^1$ even at the lowest concentration. This also suggests that the dissociation is more complex than the simple separation of DNA and protein. If the DNA unwinds in several steps, the trap *E. coli* SSB might begin binding to the partially separated DNA strand, prior to complete dissociation from the labeled *E. coli* SSB. In this case the bimolecular binding of the trap *E. coli* SSB is competing not with the bimolecular rebinding of labeled *E. coli* SSB to the DNA, but unimolecular re-wrapping of the partially separated DNA.

The helicase assays demonstrate that the MCC-*E. coli* SSB can be applied with high time resolution and sensitivity. This probe requires no cofactors and so is in the class of reagentless biosensors. Results suggest that the assay is between one and two orders of magnitude more sensitive than using tryptophan fluorescence with *E. coli* SSB [3]. The latter assay may also have limitations due to photobleaching and interference from other species that absorb in the same UV range as tryptophan. Apart from issues of sensitivity, the assay using IDCC-*E. coli* SSB has an advantage in that the fluorescence increases on forming ssDNA, making it potentially easier to measure low extents of reaction against a low fluorescence background.

The use of IDCC-SSB avoids limitations of internal tryptophan fluorescence, relating to lack of sensitivity, photobleaching, and interference from other species, such as proteins and nucleic acids that absorb in the same UV range as tryptophan. Using IDCC-SSB is between one and two orders of magnitude more sensitive than using internal tryptophan fluorescence in equivalent helicase assays, where the maximal decrease in fluorescence is to one third of the starting value, as opposed to an ~6-fold increase with IDCC-SSB. Indeed, it is easily possible to detect the unwinding of low nanomolar concentrations (in nucleotides) of DNA with good signal to noise ratio (FIG. 10*b*).

Assays based on dsDNA binding dyes can offer good sensitivity, but may result in photocleavage of the DNA substrate or inhibition of the reaction of interest [32,33]. Indeed, it was not possible to obtain a useful signal for DNA unwinding by the PcrA.RepD system using the dye displacement assay (data not shown). Moreover, the percent loading of the dye on the DNA may affect its binding and fluorescence properties due to crowding of binding sites [34]. Furthermore, there is a fluorescence decrease as ssDNA forms. In contrast, the assay using IDCC-SSB exhibits a fluorescence increase on forming ssDNA, making it easier to measure low extents of reaction against a low fluorescence background.

Practical considerations for the use of IDCC-SSB in helicase assays revolve in part on the optical properties, as outlined above. Appropriate concentrations of added IDCC-SSB will depend on the sensitivity required of the measurement, on the affinity of this protein for DNA and on a suitable ratio of SSB to DNA. At high ionic strength, the dissociation constant obtained from a titration with dT$_{70}$ is ~2.6 nM. Although this does not take into account potential cooperativity on binding to longer DNA, it gives a guide to the lower limits of concentrations. In addition, in order to obtain a relatively linear response of DNA versus fluorescence, a good working consideration is to use the equivalent of approximately one monomer of IDCC-SSB per five-base length of ssDNA. This should ensure that not only will the IDCC-SSB remain in excess over DNA whatever the binding mode, but also the signal response will have approximately a linear response, equivalent to the first part of the titrations. Like many fluorescence assays, a calibration curve may be required for complete quantitation.

IDCC-SSB can be applied with high time resolution and sensitivity to measure helicase activity in bulk solution. Because of the high sensitivity and increase in fluorescence during dsDNA unwinding, this biosensor or variants based on SSB can potentially be applied to the study of any DNA transaction involving ssDNA intermediates using bulk, high throughput or single molecule techniques.

Rhodamine-SSB Mutants (W88C)
Results

In order to take advantage of the longer wavelength and high photostability of rhodamine, a single cysteine mutant of the SSB from *E. coli* (W88C), labeled with 6-iodoacetamidotetramethylrhodamine (6-IATR), has been developed. Fluorescence enhancements of ~4.5-fold were obtained on DNA binding relative to the fluorescence in the absence of single stranded DNA.

Figure 6A:
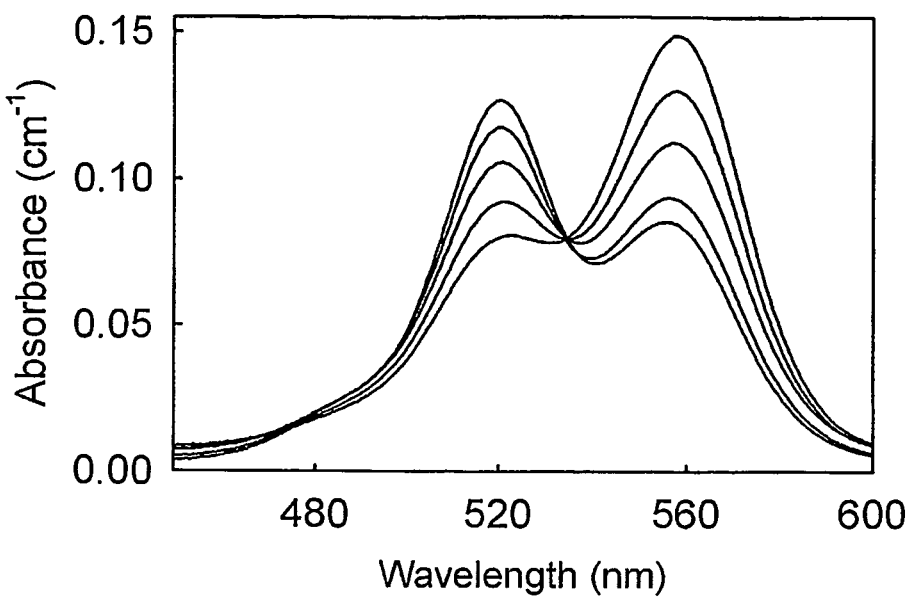
FIG. 6A shows absorbance spectra as a function of the nanomolar concentration of $dT_{70}$ (0, 124, 247, 267, 487 nM in order of increasing intensity at 560 nm). Spectra were obtained at room temperature for 0.4 µM rhodamine-*E. coli* SSB tetramers in 25 mM Tris.HCl pH 7.5, 200 mM NaCl, 1 mM DTT, and 5 µM bovine serum albumin.
Figure 6B:
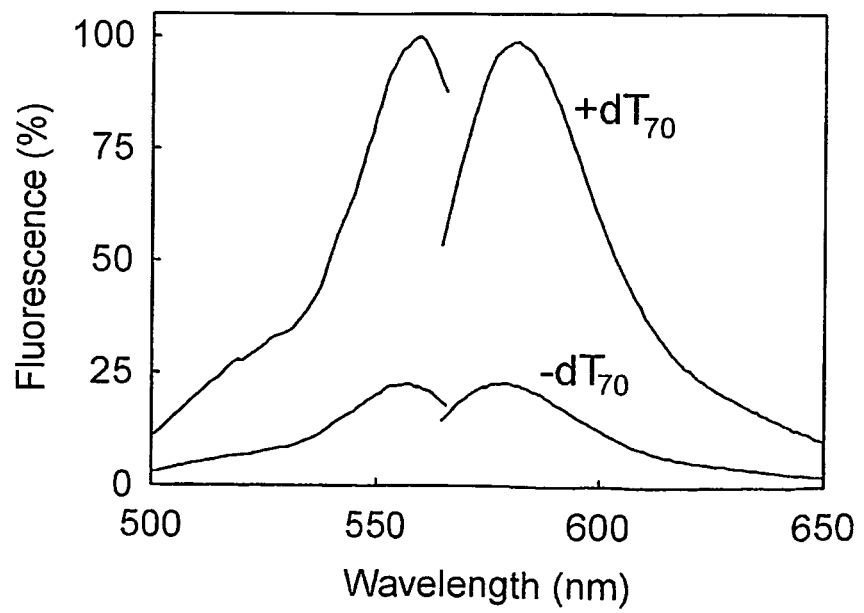
FIG. 6B shows fluorescence excitation and emission spectra of 250 nM rhodamine-*E. coli* SSB (tetramer concentration) measured at 30° C. in the same buffer, in the presence and absence of 580 nM $dT_{70}$. Excitation was at 556 nm, emission at 579 nm.

Both the fluorescence and absorbance spectra show large changes when DNA binds (FIG. 6).

The absorbance spectrum show the changes expected for a shift in monomer-dimer equilibrium for the rhodamine. The dimer ($\lambda_{max}$~520 nm) has a different absorbance spectrum from the monomer ($\lambda_{max}$ ~550 nm) and has little or no fluorescence in comparison with the monomer [35]. For this adduct, the isosbestic point is at 534 nm, 6 nm higher than for the 6-IATR-2-mercaptoethyl sulfonate adduct [36]. Thus the same extinction coefficient (52 mM$^{-1}$ cm$^{-1}$) was used but at 534 nm, in order to quantify the labeled protein.

Figure 7:
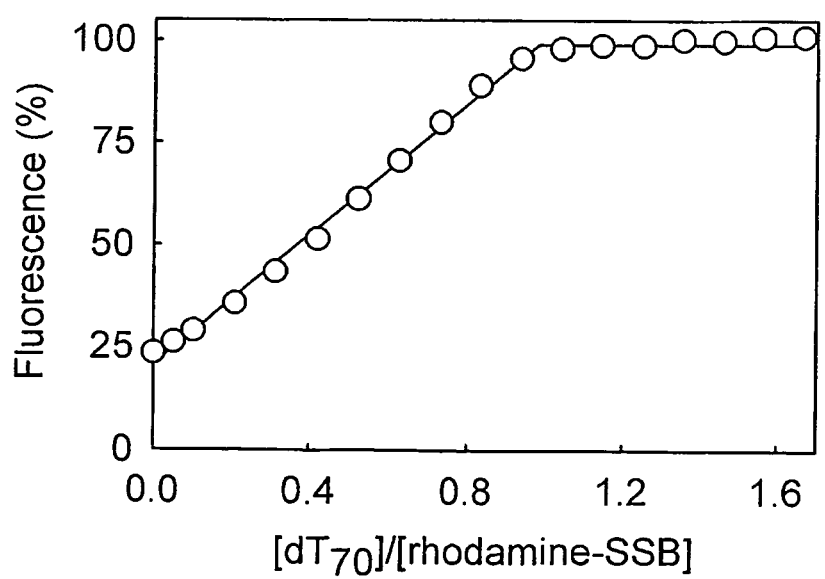
FIG. 7 shows the titration of emission intensity (excitation at 556 nm, emission 579 nm) as a function of $dT_{70}$ of rhodamine-*E. coli* SSB. 0.4 µM rhodamine-*E. coli* SSB had $dT_{70}$ added in aliquots. The lines are the best linear fit from 0-0.98 $dT_{70}$/rhodamine-*E. coli* SSB, and the best-fit horizontal line for remaining points.

The fluorescence spectra show a ~4.5-fold increase in fluorescence after addition of either dT70 (FIG. 6) or poly-dT (poly-dT consists of poly(dT) strands of various lengths, each length being approximately a few hundred bases; data not shown). A titration of dT$_{70}$ into rhodamine-*E. coli* SSB (FIG. 7) shows an approximately linear rise in fluorescence until the protein is saturated at 1:1 dT$_{70}$: *E. coli* SSB tetramer. A similar fluorescence change was seen with poly-dT (data not shown). This suggests that the fluorescence is unaffected when two tetramers are close to each other along a long piece of DNA, as opposed to one tetramer binding a 70-nucleotide length, which is the minimum length to wrap around one tetramer. The titration also shows that there is tight binding of DNA to rhodamine-*E. coli* SSB. The slight curvature is likely to be due to the small amount of unlabeled protein that binds DNA more tightly, as described above for the coumarin-labeled IDCC-*E. coli* SSB.

Discussion

The optical properties suggest that the basis for the fluorescence change with this rhodamine-*E. coli* SSB is the change in extent of stacking of two rhodamine monomers when ssDNA binds to the protein. Monomeric rhodamine has a high fluorescence quantum yield. Two rhodamine moieties, when physically close to each other and correctly oriented, can stack [37-41]. This property of rhodamines has been used previously in a number of assays and in a biosensor for inorganic phosphate, using a phosphate binding protein doubly labeled with rhodamine (rhodamine-PBP) [42]. The mechanism by which this quenching occurs through a process called exciton coupling has been discussed [43-45].

In the case of rhodamine-*E. coli* SSB, the single cysteine in each subunit gives rise to a single rhodamine. From the known crystal structures [12,13] the cysteines are positioned on β-hairpins and the hairpin of adjacent subunits are parallel and have surface contact with each other. According to these structures, this region changes little on DNA binding: the distance between Cα atoms of the two tryptophans of adjacent unmodified *E. coli* SSB protein subunits remains ~1.8 nm. In the structure with DNA bound, it seems unlikely that the two rhodamines on adjacent hairpins could stack with each other: the DNA is likely to hold these loops rigid and to create a physical barrier to the rhodamines reaching each other. The situation is less clear for the DNA-free structure. The loops may be more flexible and the lack of DNA on the surface allows more freedom of position. In addition the structure has one pair of parallel hairpins antiparallel to another pair, lying adjacent: this possibly reflects tetramer-tetramer interactions.

The rhodamine-*E. coli* SSB complements the coumarin-labeled IDCC-*E. coli* SSB. The latter has a higher fluorescence change and has the advantage that any coumarin impurity (such as doubly labeled protein or unattached coumarin) is likely to contribute only low fluorescence to the background. The higher wavelength of the rhodamine gives advantages for the optical source and photostability, although rhodamine impurities are likely to contribute high fluorescence to the background. However, without any extra purification a ~4.5-fold fluorescence change is obtained. This molecule is therefore likely to be suited to such applications as high throughput assays and single molecule studies where intense exciting light may be used.

It will be understood that the invention has been described by way of example only and modifications may be made whilst remaining within the scope and spirit of the invention.

REFERENCES

The Contents of which are Hereby Incorporated by Reference

[1] Eggleston, A. K., Rahim, N. A., and Kowalczykowski, S. C. (1996) A helicase assay based on the displacement of fluorescent, nucleic acid-binding ligands, *Nucleic Acids Res.* 24, 1179-1186.

[2] Rye, H. S., Quesada, M. A., Peck, K., Mathies, R. A., and Giazer, A. N. (1991) High-sensitivity two-color detection of double-stranded DNA with a confocal fluorescence gel scanner using ethidium homodimer and thiazole orange, *Nucl. Acids Res.* 19, 327-333.

[3] Roman, L. J., and Kowalczykowski, S. C. (1989) Characterization of the helicase activity of the *Escherichia coli* recBCD enzyme using a novel helicase assay, *Biochemistry* 28, 2863-2873.

[4] Brune, M., Hunter, J. L., Howell, S. A., Martin, S. R., Hazlett, T. L., Corrie, J. E. T., and Webb, M. R. (1998) Mechanism of inorganic phosphate interaction with phosphate binding protein from *Escherichia coli, Biochemistry* 37, 10370-10380.

[5] Tolosa, L., Gryczynski, I., Eichhorn, L. R., Dattelbaum, J. D., Castellano, F. N., Rao, G., and Lakowicz, J. R. (1999) Glucose sensor for low-cost lifetime-based sensing using a genetically engineered protein, *Anal. Biochem.* 267, 114-120.

[6] Dattelbaum, J. D., Looger, L. L., Benson, D. E., Sall, K. M., Thompson, R. B., and Helling a, H. W. (2005) Analysis of allosteric signal transduction mechanisms in an engineered fluorescent maltose biosensor, *Protein Sci.* 14, 284-291.

[7] Dwyer, M. A., and Helling a, H. W. (2004) Periplasmic binding proteins: a versatile superfamily for protein engineering, *Curr. Opin. Struct. Biol.* 14, 495-504.

[8] Moschou, E. A., Bachas, L. G., Daunert, S., and Deo, S. K. (2006) Hinge-Motion Binding Proteins: Unraveling Their Analytical Potential, *Anal. Chem.* 78, 6692-6700.

[9] Webb, M. R. (2006) Development of fluorescent biosensors for probing the function of motor proteins, *Molecular Biosystems submitted.*

[10] Murzin et al., (1995) 3 Mol Biol 247, 536-540.

[11] Lohman, T. M., and Ferrari, M. E. (1994) *Escherichia Coli* Single-Stranded DNA-Binding Protein: Multiple DNA-Binding Modes and Cooperativities, *Annual Review of Biochemistry* 63, 527-570.

[12] Raghunathan, S., Kozlov, A. G., Lohman, T. M., and Waksman, G. (2000) Structure of the DNA binding domain of *E. coli* SSB bound to ssDNA, *Nature Struct. Biol.* 7, 648-652.

[13] Raghunathan, S., Ricard, C. S., Lohman, T. M., and Waksman, G. (1997) Crystal structure of the homo-tetrameric DNA binding domain of *Escherichia coli* single-stranded DNA-binding protein determined by multiwavelength x-ray diffraction on the selenomethionyl protein at 2.9-A resolution, *Proc. Natl. Acad. Sci. U.S.A.* 94, 6652-6657.

[14] Lohman, T. M., Green, J. M., and Beyer, R. S. (1986) Large-scale overproduction and rapid purification of the *Escherichia coli* ssb gene product. Expression of the ssb gene under lambda. PL control, *Biochemistry* 25, 21-25.

[15] Kuznetsov, S. V., Kozlov, A. G., Lohman, T. M., and Ansari, A. (2006) Microsecond Dynamics of Protein-DNA Interactions: Direct Observation of the Wrapping/Unwrapping Kinetics of Single-stranded DNA around the *E. coli* SSB Tetramer, *J. Mol. Biol.* 359, 55-65.

[16] Bujalowski, W., and Lohman, T. M. (1991) Monomers of the *Escherichia coli* SSB-1 mutant protein bind single-stranded DNA, *J. Mol. Biol.* 217, 63-74.

[17] Corrie, J. E. T. (1994) Thiol-reactive fluorescent probes for protein labelling, *J. Chem. Soc. Perkin Trans. I,* 2975-2982.

[18] Fletcher, A. N., and Bliss, D. E. (1978) Laser dye stability. Part 5. Effect of chemical substituents of bicyclic dyes upon photodegradation parameters, *Appl. Phys.* 16, 289-295.

[19] Leatherbarrow, R. J. (2001) *Grafit Version* 5, Erithacus Software Ltd., Horley, U.K.

[20] Zhang, W., M: S. Dillingham, C. D. Thomas, S. Allen, C. J. Roberts, and P. Soultanas. 2007. Directional loading and stimulation of PcrA helicase by the replication initiator protein Rep D. J. Mol. Biol. 371:336-348.

[21] Yeeles, J. T. P., and M. S. Dillingham. 2007. A dual-nuclease mechanism for DNA break processing by AddAB-type helicase-nucleases. J. Mol. Biol. 371:66-78.

[22] Singleton, M. R., M. S. Dillingham, M. Gaudier, S. C. Kowalczykowski, and D. B. Wigley. 2004. Crystal structure of RecBCD enzyme reveals a machine for processing DNA breaks. Nature 432:187-193.

[23] Webb, M. R., and Corrie, J. E. T. (2001) Novel coumarin-labeled analogues of purine nucleotides as fluorescent probes of the actomyosin ATPase, *Biophys. J.* 80, 76a.

[24] Dillingham, M. S., Webb, M. R., and Kowalczykowski, S. C. (2005) Bipolar DNA translocation contributes to highly processive DNA unwinding by RecBCD enzyme, *J. Biol. Chem.* 280, 37069-37077

[25] Roman, L. J., and S. C. Kowalczykowski. 1989. Characterization of the helicase activity of the *Escherichia coli* RecBCD enzyme using a novel helicase assay. Biochemistry 28:2863-2873.

[26] Bianco, P. R., L. R. Brewer, M. Corzett, R. Balhorn, Y. Yeh, S. C. Kowalczykowski, and R. J. Baskin. 2001. Processive translocation and DNA unwinding by individual RecBCD enzyme molecules. Nature 409:374-377.

[27] Dillingham, M. S., M. R. Webb, and S. C. Kowalczykowski. 2005. Bipolar DNA translocation contributes to highly processive DNA unwinding by RecBCD enzyme. J. Biol. Chem. 280:37069-37077.

[28] Thomas, C. D., D. F. Balson, and W. V. Shaw. 1990. In vitro studies of the initiation of Staphylococcal plasmid replication. Specificity of RepD for its origin (oriD) and characterization of the RepD-ori tyrosyl ester intermediate. J. Biol. Chem. 265:5519-5530.

[29] Soultanas, P., M. S. Dillingham, F. Papadopoulos, S. E. Phillips, C. D. Thomas, and D. B. Wigley. 1999. Plasmid replication initiator protein RepD increases the processivity of PcrA DNA helicase. Nucleic Acids Res. 27:1421-1428.

[30] Chedin, F., and S. C. Kowalczykowski. 2002. A novel family of regulated helicases/nucleases from Gram-positive bacteria: insights into the initiation of DNA recombination. Mol. Microbiol. 43:823-834.

[31] Kozlov, A. G., and Lohman, T. M. (2002) Stopped-Flow Studies of the Kinetics of Single-Stranded DNA Binding and Wrapping around the <i>Escherichia coli </i>SSB Tetramer, Biochemistry 41, 6032-6044.

[32] Akerman, B., and E. Tuite. 1996. Single- and double-strand photocleavage of DNA by YO, YOYO and TOTO. Nucleic Acids Res. 24:1080-1090.

[33] OhUigin, C., D. J. McConnell, J. M. Kelly, and W. J. M. van der Putten. 1987. Methylene blue photosensitised strand cleavage of DNA: effects of dye binding and oxygen. Nucleic Acids Res. 15:7411-7427.

[34] Carisson, C., M. Johnson, and B. Akerman. 1995. Double bands in DNA gel electrophoresis caused by bis-intercalating dyes. Nucleic Acids Res. 23:2413-2420.

[35] Chambers, R. W., Kajiwara, T., and Kearns, D. R. (1974) Effect of dimer formation on the electronic absorption and emission spectra of ionic dyes, J. Phys. Chem. 78, 380-387

[36] Corrie, J. E. T., and Craik, J. S. (1994) Synthesis and characterisation of pure isomers of iodoacetamidotetramethylrhodamine, J. Chem. Soc. Perkin Trans. I, 2967-2974.

[37] Förster, T., and König, E. (1957) Absorptionsspektren and Fluoreszenzeigenschaften konzentrierter Lösungen organischer Farbstoffe, Z. Elektrochem. 61, 344-348.

[38] Selwyn, J. E., and Steinfeld, J. I. (1972) Aggregation equilibria of xanthene dyes, J. Phys. Chem. 76, 762-774.

[39] Geoghegan, K. F., Rosner, P. J., and Hoth, L. R. (2000) Dye-pair reporter systems for protein-peptide molecular interactions, Bioconjugate Chem. 11, 71-77.

[40] Blackman, M. J., Corrie, J. E. T., Croney, J. C., Kelly, G., Eccleston, J. F., and Jameson, D. M. (2002) Structural and biochemical characterization of a fluorogenic rhodamine-labeled malarial protease substrate, Biochemistry 41, 12244-12252.

[41] Packard, B. Z., Toptygin, D. D., Komoriya, A., and Brand, L. (1996) Profluorescent protease substrates: intramolecular dimers described by the exciton model, Proc. Natl. Acad. Sci. U.S.A. 93, 11640-11645.

[42] Okoh, M. P., Hunter, J. L., Corrie, J. E. T., and Webb, M. R. (2006) A biosensor for inorganic phosphate using a rhodamine-labeled phosphate binding protein, Biochemistry 45, 14764-14771.

[43] Kasha, M. (1963) Energy transfer mechanisms and the molecular exciton model for molecular aggregates, Radiat. Res. 20, 55-70.

[44] Kasha, M., Rawls, H. R., and Ashraf El-Bayoumi, M. (1965) The exciton model in molecular spectroscopy, Pure Appl. Chem. 11, 371-392.

[45] Scholes, G. D., and Ghiggino, K. P. (1994) Electronic interactions and interchromophore electron transfer, J. Phys. Chem. 98, 4580-4590.

The invention claimed is:

1. A labeled protein comprising one of the following sequences:

amino acids 2-178 of SEQ ID NO: 1 wherein at least one amino acid of positions 27, 89 or 93 is substituted with a fluorescently labeled cysteine;

amino acids 2-162 of SEQ ID NO: 7 wherein at least one amino acid of positions 27 and 89 is substituted with a fluorescently labeled cysteine;

amino acids 2-175 of SEQ ID NO: 8 wherein at least one amino acid of positions 27 and 89 is substituted with a fluorescently labeled cysteine;

amino acids 2-170 of SEQ ID NO: 9 wherein at least one amino acid of positions 23 and 82 is substituted with a fluorescently labeled cysteine;

amino acids 2-152 of SEQ ID NO: 10 wherein at least one amino acid of positions 22 and 83 is substituted with a fluorescently labeled cysteine;

amino acids 2-162 of SEQ ID NO: 11 wherein at least one amino acid of positions 26 and 88 is substituted with a fluorescently labeled cysteine; and amino acids 2-179 of SEQ ID NO: 12 wherein at least one amino acid of positions 23 and 82 is substituted with a fluorescently labeled cysteine;

and wherein the fluorescent label emits a signal that is greater when the labeled protein is bound to single-stranded DNA as compared to when the labeled protein is not bound to single-stranded DNA.

2. The labeled protein according to claim 1, wherein the labeled protein has an amino acid sequence selected from the group consisting of SEQ ID NO: 2, SEQ ID NO: 3 and SEQ ID NO: 4.

3. The labeled protein of claim 1, wherein the fluorescent label is a coumarin.

4. The labeled protein of claim 1, wherein the fluorescent label is a rhodamine.

5. The labeled protein according to claim 1, wherein the fluorescent label is selected from the group consisting of N-[2-(iodoacetamido)ethyl]-7-diethylaminocoumarin-3-carboxamide, 2-(4'maleimidylanilino)naphthalene-6-sulfonic acid, N-[2-(1-maleimidyl)ethyl]-7-diethylaminocoumarin-3-carboxamide, Alexa Fluor 488, Alexa Fluor 546 and 6-iodoacetamidotetramethylrhodamine.

6. The labeled protein according to claim 5, wherein the fluorescent label is 2-(4'maleimidylanilino)naphthalene-6-sulfonic acid.

7. The labeled protein according to claim 5, wherein the fluorescent label is 6-iodoacetamidotetramethylrhodamine.

8. A method for detecting single stranded DNA in a sample comprising the steps of:
(i) mixing a sample comprising single stranded DNA with the labeled protein of claim 1, and
(ii) detecting a change in the signal from the labeled protein arising from an interaction between the single stranded DNA and the labeled protein and thereby detecting single stranded DNA in the sample.

9. A method of screening for an inhibitor of a DNA processing enzyme
comprising
contacting the labeled protein of claim 1 with a cell in the presence of compound and measuring a first single stranded DNA level,
contacting the labeled protein with a cell in the absence of the compound and measuring a second single stranded DNA level, and
comparing the first single stranded DNA level to the second single stranded DNA level, wherein if the second single stranded DNA level is greater than the first single stranded DNA level, then the compound is an inhibitor of a DNA processing enzyme.

* * * * *